US006810405B1

(12) United States Patent
LaRue et al.

(10) Patent No.: US 6,810,405 B1
(45) Date of Patent: Oct. 26, 2004

(54) SYSTEM AND METHODS FOR SYNCHRONIZING DATA BETWEEN MULTIPLE DATASETS

(75) Inventors: Chris LaRue, Santa Cruz, CA (US); Jeff Gray, Capitola, CA (US); Roy W. Feague, Scotts Valley, CA (US)

(73) Assignee: Starfish Software, Inc., Scotts Valley, CA (US)

( * ) Notice: Subject to any disclaimer, the term of this patent is extended or adjusted under 35 U.S.C. 154(b) by 654 days.

(21) Appl. No.: 09/679,944

(22) Filed: Oct. 4, 2000

Related U.S. Application Data

(63) Continuation-in-part of application No. 09/311,781, filed on May 13, 1999, now Pat. No. 6,487,560, and a continuation-in-part of application No. 09/208,815, filed on Dec. 8, 1998, now Pat. No. 6,477,545, and a continuation-in-part of application No. 09/136,215, filed on Aug. 18, 1998, now Pat. No. 6,295,541.

(60) Provisional application No. 60/226,446, filed on Aug. 17, 2000, and provisional application No. 60/158,481, filed on Oct. 8, 1999.

(51) Int. Cl.[7] ............................................. G06F 17/30
(52) U.S. Cl. ........................ 707/201; 707/200; 707/10; 709/203
(58) Field of Search ........................ 707/10, 200, 201, 707/202, 104.1; 709/203

(56) References Cited

U.S. PATENT DOCUMENTS 5,588,147 A    12/1996    Neeman et al. ................. 707/1

(List continued on next page.)

Primary Examiner—Greta Robinson
Assistant Examiner—Cheryl Lewis
(74) Attorney, Agent, or Firm—Ernest J. Beffel, Jr.; Haynes Beffel & Wolfeld LLP

(57) ABSTRACT

Methods for synchronizing PIM data between a wireless telephone and a synchronization server. A communication in interface is established between the telephone and the server, using a wireless network and the Internet. The telephone initiates the synchronization by placing a data call to the server and logging on to the server. A sync client within the telephone sends recent changes to its dataset to the server and requests an acknowledgement of these changes. In an acknowledgement message, the server specifies which changes were actually received. Based on this acknowledgment, the client continues resending changes until it receives confirmation that the server has received all of its changes. The server performs conflict and duplicate resolution between the changes received from the client and other changes of which the server is aware, and enters into its dataset those changes that survive the resolutions. The client also requests that the server send changes that have been made to the server's dataset. The server identifies all changes that should be sent to the client and that have survived the conflict and duplicate resolutions. The server then sends its changes to the client, requests acknowledgement, and resends changes until it confirms that the client has received all of the changes. The client enters the changes from the server into its dataset without any further conflict or duplicate resolution. The client then logs off of the server and ends the data call.

39 Claims, 11 Drawing Sheets

U.S. PATENT DOCUMENTS

| | | | |
|---|---|---|---|
| 5,600,834 A | 2/1997 | Howard | 707/201 |
| 5,675,802 A | 10/1997 | Allen et al. | 717/103 |
| 5,787,262 A * | 7/1998 | Shakib et al. | 709/205 |
| 5,806,074 A * | 9/1998 | Souder et al. | 707/201 |
| 5,845,293 A | 12/1998 | Veghte et al. | 707/202 |
| 5,870,759 A * | 2/1999 | Bauer et al. | 707/201 |
| 5,870,765 A | 2/1999 | Bauer et al. | 707/203 |
| 5,884,323 A | 3/1999 | Hawkins et al. | 707/201 |
| 5,884,325 A | 3/1999 | Bauer et al. | 707/201 |
| 5,974,238 A * | 10/1999 | Chase, Jr. | 709/248 |
| 6,006,331 A * | 12/1999 | Chu et al. | 713/201 |
| 6,029,178 A | 2/2000 | Martin et al. | 707/201 |
| 6,049,809 A | 4/2000 | Raman et al. | 707/203 |
| 6,115,394 A * | 9/2000 | Balachandran et al. | 370/477 |
| 6,212,529 B1 | 4/2001 | Boothby et al. | 707/201 |
| 6,289,357 B1 | 9/2001 | Parker | 707/202 |
| 6,295,541 B1 | 9/2001 | Bodnar et al. | 707/203 |
| 6,304,881 B1 * | 10/2001 | Halim et al. | 707/201 |
| 6,370,566 B2 * | 4/2002 | Discolo et al. | 709/206 |

* cited by examiner

SYSTEM AND METHODS FOR SYNCHRONIZING DATA BETWEEN MULTIPLE DATASETS

RELATED APPLICATIONS

This application claims the benefit of U.S. Provisional Application No. 60/226,446, filed Aug. 17, 2000, and U.S. Provisional Application No. 60/158,481, filed Oct. 8, 1999; and this application is a continuation in part of U.S. application Ser. No. 09/311,781, U.S. Pat. No. 6,487,560, filed May 13, 1999, a continuation in part of U.S. application Ser. No. 09/208,815, filed Dec. 8, 1998 and a continuation in part of U.S. application Ser. No. 09/136,215, U.S. Pat. No. 6,295,541, filed Aug. 18, 1998. This application is related to the following commonly-owned U.S. patent applications, the disclosures of which are hereby incorporate by reference in their entirety, including any appendices or attachments thereof, for all purposes:

Ser. No. 60/226,446 filed Aug. 17, 2000 and entitled SYSTEM AND METHODS FOR SYNCHRONIZING DATA BETWEEN MULTIPLE DATASETS;

Ser. No. 60/158,481, filed Oct. 8, 1999 and entitled WIRELESS COMMUNICATION DEVICE AND SYNCHRONIZATION SERVER WITH METHODS FOR SYNCHRONIZING USER DATASETS;

Ser. No. 09/369,812 U.S. Pat. No. 6,658,268, filed Aug. 6, 1999 and entitled ENHANCED COMPANION DIGITAL ORGANIZER For a Cellular Phone Device;

Ser. No. 09/311,781 U.S. Pat. No. 6,487,560 filed May 13, 1999 and entitled SYSTEM AND METHODS FOR SYNCHRONIZING DATASETS IN A NON-FIFO OR OTHERWISE DIFFICULT COMMUNICATION ENVIRONMENT, as a continuation in part;

Ser. No. 09/208,815, U.S. Pat. No. 6,477,545 filed Dec. 8, 1998 and entitled SYSTEM AND METHODS FOR ROBUST SYNCHRONIZATION OF DATASETS, as a continuation in part; and Ser. No. 09/136,215, U.S. Pat. No. 6,295,541 filed Aug. 18, 1998 and entitled SYSTEM AND METHODS FOR SYNCHRONIZING TWO OR MORE DATASETS, as a continuation in part.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND OF THE INVENTION

The present invention relates generally to synchronizing data between multiple datasets. More particularly, the present invention relates to methods for synchronizing data between mobile wireless communication devices and synchronization servers.

Increasingly, people are discovering the power of computer-based personal information managers (PIMs) for managing appointments and other personal information such as tasks ("to-do's") and addresses. Individuals employ PIMs for example on personal computers (PCs), handheld electronic information devices, and World Wide Web servers accessed via browsers. Examples of PC-based PIMs include the Sidekick® software application, which is available from Starfish® Software, Inc. ("Starfish"), the present assignee. Examples of handheld-information-device-based PIMs include the StarTAC® clipOn Organizer device and the REX PRO™ organizer device—both of which include licensed technology from Starfish—as well as the popular Palm family of organizer devices. Examples of "Web-based" PIMs include an online PIM called TrueSync.com, provided by Starfish. Starfish®, Sidekick®, and TrueSync® are registered trademarks of Starfish. StarTAC® is a registered trademark of Motorola, Inc. of Schaumburg, Ill. REX™ m and REX PRO™ are trademarks of Franklin Electronic Publishers of Burlington, N.J. Palm organizers are produced by Palm, Inc. of Santa Clara, Calif.

The use of PIMs is ever expanding, and it has become common for an individual person to keep multiple "copies" of the same information on separate devices. For example, a user may keep his or her appointments in a dataset (i.e., collection of data) on a desktop PC at work, in a dataset on a notebook PC at home, and also in a dataset on a handheld device while in the field. Such a user is free to change the information in any one of these datasets independently of the other datasets. By doing so, the user may cause the data in the multiple datasets to differ from one another, so that the datasets are unsynchronized. For example, the user may enter a person's home address in one of the datasets, but the other datasets may not contain the person's home address. Alternatively, the user may change a person's telephone number in one of the datasets, so that the one dataset has the user's new telephone number, while the other datasets have the person's old telephone number. The user may cause the datasets to be the same again, by synchronizing the multiple datasets to bring them back into equivalence. To perform such synchronization, the user generally uses a synchronization system, such as one that is described in commonly-owned U.S. Pat. No. 5,519,606, which is hereby incorporated by reference.

As modern mobile wireless communication devices, such as pagers and cellular phones, are gaining capabilities and becoming information devices in their own right, e.g. by supporting PIM functionality, it is desirable for such devices to also support synchronization of information (e.g. PIM information, downloaded information, and the like) stored on the device. In particular, it is desirable that such wireless communication devices use their inherent wireless communication abilities for synchronization.

Many existing synchronization systems exchange data over a direct, wired connection between two devices, which provides a fast, accurate and reliable interface between the two devices. Exchanging data over a wireless interface is generally not so easy or predictable. Errors are more likely to occur during transmission of data over a wireless interface, communication sessions may be interrupted, data packets may be lost, data transmission may be delayed or slow, data transmissions may be intercepted by eavesdroppers, data may arrive at its destination in a different order from the order in which it was sent from its source, and many other problems may adversely affect the wireless transmission of data. Many existing synchronization systems may not work effectively in such an environment. In addition, wireless devices generally have limited processing, capabilities and storage space, and limited access to software upgrades, which further complicates the process for synchronizing data with a wireless device.

What is needed are a wireless communication system and methods for managing synchronization between a wireless communication device and a synchronization server. In particular, what is needed are such a system and methods that are efficient, cost-effective, and convenient for the user, that work within the processing, storage and upgrade limitations of a wireless device, and that will work effectively and reliably in a wireless environment.

BRIEF SUMMARY OF THE INVENTION

The present invention provides methods for synchronizing data between multiple datasets on multiple devices. In one method, a communication interface, including a wireless interface, is established between a first device and a second device. The first device sends its changed data values to the second device. The second device resolves conflicts between the changed data values received from the first device and the second device's own changed data values. The second device incorporates the changed data values received from the first device into its own dataset if the received data values survive the conflict resolution. The second device also sends those of its own changed data values that survived the conflict resolution to the first device. The first device incorporates the changed data values that it receives from the second device into the first dataset.

In specific embodiments of the present invention, the multiple devices may include a wireless telephone and a sync server, and the communication interface may comprise a data call between the wireless telephone and the sync server. The datasets may contain PIM data and one or more of the multiple devices may include a PIM application. In one embodiment, one device may need to log on to the second device before a synchronization can be performed, where logging on requires that the first device send log on information to the second device and the second device confirms that the log on information is valid. In another embodiment, a conflict resolution may occur between two changed data values if both of the changes relate to the same data record. In this case, timestamps indicating the times at which each of the data values were changed may be compared, and data from the earlier changed data value may be discarded, and the more recently changed data value may survive the conflict resolution.

Other embodiments of the invention may include a method of sending data value changes from a first device to a second device that involves repeating the following steps until the second device receives all of the data value change from the first device: the first device sends to the second device one or more changes from its set of data value changes that have not yet been received by the second device; the second device sends a message to the first device acknowledging receipt of whichever changes the second device actually received; and the first device determines which, if any, of its set of data value changes have not yet been received by the second device, based on the acknowledgement message from the second device. In one embodiment, the second device sends the acknowledgment message in response to an acknowledgment request sent from the first device to the second device. Other embodiments may also involve the first device determining if a change received from the second device involves creating a new data record in the first device and, if so, sending a message to the second device indicating the record ID within the first device for the new data record. Also, some embodiments may include duplicate resolution between the data values changes of the first device and the data value changes of the second device.

These synchronization methods may be initiated in response to various occurrences, such as in response to a user of one of the devices activating a synchronization key or otherwise specifically activating a synchronization function, in response to a timer interrupt indicating the expiration of a time interval or the reaching of a specific time of day, or in response to a user entering a data value change at one of the devices. Also, in some embodiments, the devices may send data value changes and other messages in the form of data packets in a packet switching network. In some embodiments, before a first device sends its data value changes to a second device, the first device may determine whether a previous synchronization attempt was not completed successfully and, if a previous attempt was not completed successfully, the first device may complete the previous synchronization attempt.

In one embodiment of the present invention, each of two devices sends data value changes to the other device in response to receiving one or more data value changes, and one of the two devices may resolve conflicts between its own dataset and data value changes received from the other device, as it receives those changes from the other device. In this embodiment, each of the multiple devices may receive changes from users of the device or it may receive changes from other devices. In one embodiment, in response to a change being made at a second device, the second device sends a message to a first device indicating that the second device has a chance for the dataset of the first device and the second device awaits a message from the first device requesting that the second device send the change, before the second device sends the change to the first device. In another embodiment, each of two devices may perform conflict resolution between its own dataset and data value changes received from the other of the two devices.

DETAILED DESCRIPTION OF THE INVENTION

Figure 1:
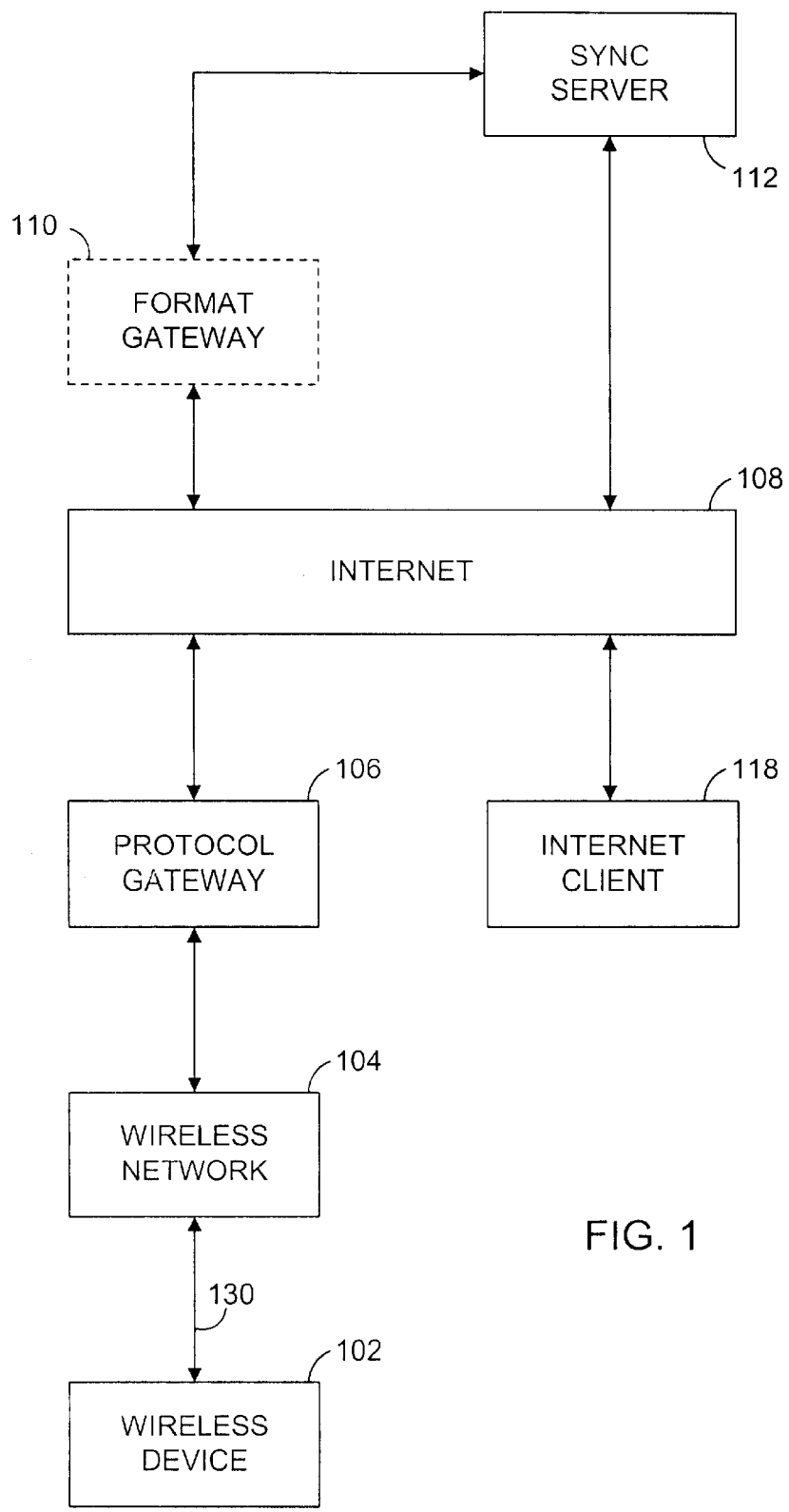
FIG. 1 is a functional block diagram of a communication system in which the preferred embodiment of the present invention may be implemented.

FIG. 1 is a functional block diagram of a communication system in which the preferred embodiment of the present invention may be implemented. The system comprises a wireless communication device 102, a wireless network 104, a protocol gateway (or interworking gateway) 106, the Internet 108, an optional format gateway 110, a synchronization (sync) server 112, and an Internet client 118.

The wireless device 102 may be, for example, a wireless telephone, a personal digital assistant (PDA), a pager, or a notebook computer with a wireless interface. In particular, the wireless device 102 may be any of a number of currently available wireless telephones that have a programmable microprocessor, and sufficient processing capabilities, memory and other resources to add software routines implementing the methods of the present invention. The present invention may also be implemented in an existing wireless telephone by, adding a microprocessor and additional memory to the existing resources of the telephone, so that the existing resources can perform traditional wireless telephone functions, such as call control functions, while the added resources can perform the functions of the present invention.

The wireless device 102 may be, for example, a smart cellular phone device that contains cellular calling capability, two-way paging capability, and PIM functionality. The wireless device 102 may be, for example, an integrated cellular phone built on the V-Series flip-style phone, available from Motorola, Inc., the corporate parent company of Starfish Software, the present assignee. More particularly, the wireless device 102 may be a V-Series flip-style phone that has been modified to include internally a version of the user interface and PIM of the StarTAC® clipOn Organizer device that includes licensed technology from Starfish Software, and which is further described in the incorporated and commonly-owned U.S. patent application having Ser. No. 09/369,812, U.S. Pat. No. 6,658,268 filed Aug. 6, 1999 and entitled ENHANCED COMPANION DIGITAL ORGANIZER FOR A CELLULAR PHONE DEVICE.

The wireless network 104 may be any wireless communication system. For example, the wireless network 104 may be a cellular or personal communications services (PCS) system based on any of the various wireless technologies, such as a Global System for Mobile (GSM) communication system, a code division multiple access (CDMA) system, a time division multiple access (TDMA) system, or any other wireless telephone system, or a paging or other wireless messaging or communication system, such as the FLEX paging network or a GSM communication network's Short Message Service (SMS) functional component. The wireless network 104 may also be an implementation of a third generation wireless system or other future wireless system. The wireless network 104 may comprise, for example, antennas, base stations and mobile switching centers, as is well known in the art. The wireless device 102 communicates with the wireless network 104 over a wireless interface 130, according to the particular requirements of the wireless network 104. The wireless network 104 routes calls (including both voice and data calls) and/or messages, or data packets, or other data between the wireless device 102 and other networks, such as the public switched telephone network (PSTN), the Internet 108 and other wireless networks.

In the preferred embodiment of the present invention, the wireless network 104 is a digital cellular or PCS system, such as a GSM system. Existing digital wireless systems allow for the transmission of data through data calls or through messages, such as in a system that provides SMS functionality. A data call is a circuit-switched or connection-oriented interface, as opposed to a packet-switched or connectionless interface. A person of skill in the art will appreciate the distinction between a connection-oriented interface and a connectionless interface, as the distinction is described in great detail in various references related to voice and data networking. In a connection-oriented interface, a communication channel is established between two parties that will exchange data. For example, in a TDMA system, a specific timeslot of a specific frequency channel is set aside for the purpose of transmitting data between the two parties for the duration of the data call. The network resources represented by this communication channel are entirely consumed for the duration of the data call, even if there are significant pauses in the transmission of data. The network resources cannot be used for any other purpose until the data call is terminated. An example of a connection-oriented environment is a conventional telephone (i.e., voice) system, such as the PSTN. Current wireless communication systems provide circuit switching for both voice and data calls.

Wireless service providers are currently developing packet-switched technology for their wireless networks. For example, the general packet radio service (GPRS) is being developed for GSM networks. In a packet-switched environment, communication channels are not dedicated to the exchange of data between specific parties. Instead, any party in the network may generally exchange data with any other party in the network (or in a connected network) at any time, by directing one or more packets of data to the network address of the receiving party. Examples of packet-switched environments are a local area network and the Internet. Once wireless service providers add packet-switching technology to their wireless networks, a wireless device will be able to send data packets to any of various networked devices by specifying the network address of the device. For example, a wireless device will be able to send a data packet to an Internet application by specifying the application's uniform resource locator (URL). Conversely, an Internet application may send data to the wireless device by specifying the URL of the wireless device. This exchange of data packets may occur without establishing a data call between the wireless device and the Internet application. Thus, the network resources used to send these data packets are available to other parties in between the times that data packets for these two parties are being transmitted. Once wireless packet switching networks are widely available, the present invention can take advantage of the efficiencies of sending data packets, instead of tying up a communication channel for the duration of a data call.

Until packet-switched wireless networks are available, limited connectionless communications may be achieved by using messaging services, such as SMS. Thus, the wireless network 104 may provide both connection-oriented and connectionless capabilities. Although current connectionless capabilities may be limited to a messaging service, future wireless networks may provide more robust packet-switched wireless networks. When more robust connectionless communications are available, they will be preferred over more limited messaging services. The present invention may be implemented to use connection-oriented communications or connectionless communications, or both communication technologies simultaneously or alternatively, in various ways, as will be described in greater detail below.

Typically, a wireless service provider installs and manages the wireless network 104. The wireless service provider will typically also provide the protocol gateway 106. The protocol gateway 106 may comprise a wireless application protocol (WAP) gateway or proxy. The protocol gateway 106 provides an interface between the wireless network 104 and other networks, such as the PSTN, the Internet 108, and other wireless networks. The protocol gateway 106 may comprise an application running on a PC that is configured to operate as a server. The protocol gateway 106 may provide, for example, a modem function to interface the wireless network 104 with the PSTN. The protocol gateway 106 may also provide a direct digital interface between the wireless network 104 and the Internet 108. Interfacing the wireless network 104 with the Internet 108 involves translating communications between the protocol stack of the wireless device 102 and the protocol stack of the Internet 108. In the preferred embodiment, the wireless device 102 uses the WAP protocol stack defined by the WAP Forum and specified in documents that can be found on the Internet. The protocol stack of the Internet 108 comprises the transmission control protocol/Internet protocol (TCP/IP) and the hypertext transfer protocol (HTTP) of the World Wide Web (WWW). For an introduction to TCP/IP, see e.g., RFC 1180. A TCP/IP Tutorial, the disclosure of which is hereby incorporated by reference. A copy of RFC 1180 is currently available on the Internet at the ftp.isi.edu/in-notes/rfc1180.txt. Further description of HTTP is available in the technical and trade literature; see e.g., William Stallings, *The Backbone of the Web*, BYTE, October 1996, the disclosure of which is hereby incorporated by reference. So, in the preferred embodiment of the present invention, the protocol gateway 106 converts data between the WAP protocol stack of the wireless device 102 and the TCP/IP protocols of the Internet 108. The protocol gateway 106 may also convert data between the wireless transfer protocol (WTP) of the WAP protocol stack to the HTTP protocol. The lower levels of the protocol stack of the wireless device 102 may vary, depending on the technology of the particular wireless network 104. For example, the protocol stack will vary, depending on whether the wireless network 104 implements a GSM system, a CDMA system or a TDMA system, for example. Some wireless service providers already have protocol gateways 106 that provide their wireless telephone users with access to the Internet 108.

The sync server 112 is preferably a server-based application that provides synchronization capabilities, as well as a PIM function. The sync server 112 may be located on a local area network (LAN) or on the Internet 108, for example. The sync server 112 may be, for example, an adaptation of an existing Internet-based server application, such as TrueSync.com or the Excite Planner. The sync server 112 employs standard Internet content formats and protocols, such as the hypertext markup language (HTML), the JavaScript scripting language, HTTP, and TCP/IP. Further description of HTML documents is available in the technical and trade literature; see e.g., Ray Duncan, *Power Programming: An HTML Primer*, PC Magazine, Jun. 13, 1995, the disclosure of which is hereby incorporated by reference. Consequently, the sync server 112 may be accessed by an ordinary Internet client 118. The client 118 may be, for example, a PC running a standard web browser, and connected to the Internet in a conventional manner, such as by a telephone modem to an Internet service provider.

The wireless device 102 preferably employs WAP content formats defined by the WAP Forum and specified in documents that can be found on the world wide web at a site wapforum.org, such as a binary wireless markup language (WML) format and WMLScript. The optional format gateway 110 converts content between the Internet formats employed by the sync server 12 and the WAP formats of the wireless device 102. The format gateway 110 may also comprise an application running on a PC configured to operate as a server. Various format gateways 110 (or WAP gateways) have already been designed and implemented on the Internet 108. The format gateway 110 may alternatively be placed at other locations within the communication system, such as between the protocol gateway 106 and the Internet 108. The format gateway 110 may also be integrated into, or with, the wireless network 104, the protocol gateway 106, or the sync server 112. In particular, the function of the format gateway 110 may be integrated into a parser 308 (see FIG. 3) of the sync server 112, so that communications from the wireless device 102 are transmitted all the way to the sync server 112 in the WAP content formats, and then converted by the parser 308 directly from the WAP content formats into a format that is understood by the sync server 112 (such as, for example, a proprietary format), without first converting the content into Internet formats.

In summary, there are three basic functions that may be performed by the protocol gateway 106 and the format gateway 110 to enable communications between the wireless device 102, which preferably uses the WAP protocols and content formats, and the sync server 112, which preferably uses the Internet protocols and content formats. First, if the data is to be transmitted over the Internet 108, then there must be a conversion between the WAP protocol stack and the TCP/IP protocols used by the Internet 108. Second, if the sync server 112 uses the HTTP protocol and the wireless device 102 uses the WTP protocol, then there must be a conversion between the WTP protocol of the wireless device 102 and the HTTP protocol of the sync server 112. Third, if the sync server 112 uses the data content formats of the Internet 108 and if the wireless device 102 uses the WAP data content formats, then there must be a conversion between these content formats, such as between the WML format and the HTML format. So, depending on the needs of the sync server 112 and the wireless device 102, one or more of these functions may be implemented in the communication system of FIG. 1. The system designer has great flexibility in deciding which functions will be implemented and how and where they will be implemented. For example, if the sync server 112 is designed to use the WTP protocol of the wireless device 102, the wireless device 102 is designed to use a proprietary data content format of the sync server 112, and the data will be transmitted over the Internet 108, then the only required conversion would be a conversion by the protocol gateway 106 between the WAP protocol stack of the wireless device 102 and the TCP/IP protocols of the Internet 108.

Most of the communication system illustrated in FIG. 1 already exists. Wireless service providers currently provide the wireless network 104 and the protocol gateway 106. Of course, the Internet 108 already exists. The Internet client 118 can easily be purchased from various computer retailers, and access to the Internet 108 can be provided by various Internet service providers. The format gateway 110 already exists. Alternatively, a customized format gateway 110 can be readily designed by a person of skill in the art. The wireless device 102 may be any of various existing cellular telephones that can be loaded with software that implements the wireless device methods of the present invention, or that can be modified, as described above, to add an additional microprocessor and additional memory to implement the wireless device methods of the present invention. Finally, the sync server 112 can be modeled after existing Internet-based PIMs that have synchronization capabilities, by adding additional software to implement the sync server methods of the present invention. Thus, the primary chances required to realize the present invention in existing communication systems involve adding software (and possibly hardware) to an existing wireless device and to existing Internet-based PIMs to implement the methods of the present invention. Alternatively, various aspects of the communication system illustrated in FIG. 1 may be modified when implementing the current invention. The wireless device 102, the sync server 112, and the format gateway 110, in particular, may be redesigned to better implement the present invention.

Figure 2:
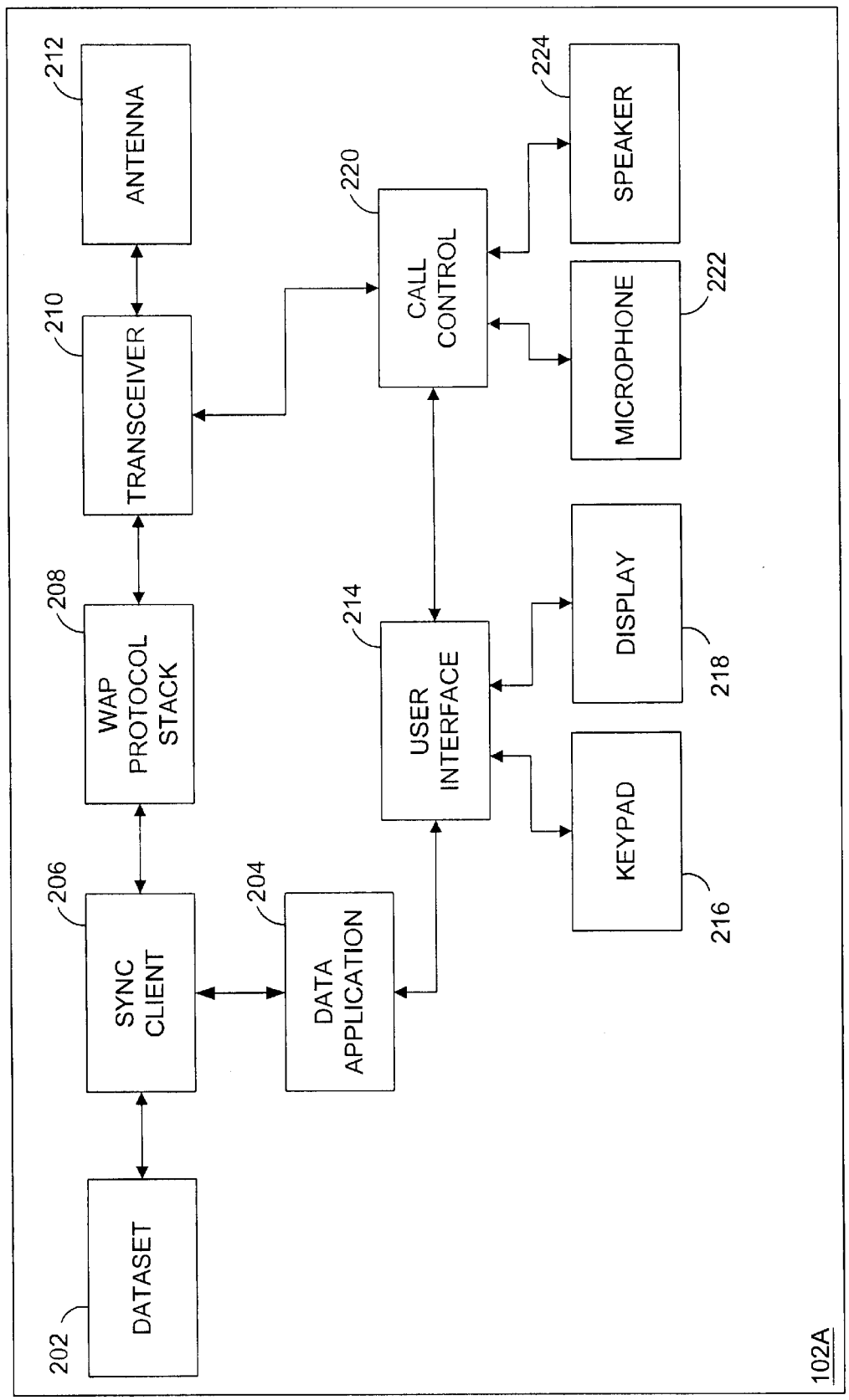
FIG. 2 is a functional block diagram of a wireless communication device that may be used in the preferred embodiment of the present invention.

FIG. 2 is a functional block diagram of a wireless telephone 102A that may be used in the present invention as the wireless device 102. The wireless telephone 102A preferably comprises a dataset 202, a data application 204, a sync client 206, a WAP protocol stack 208, a transceiver 210, an antenna 212, a user interface 214, a keypad 216, a display 218, a call control routine 220, a microphone 222 and a speaker 224.

The user interface 214, the keypad 216, the display 218, the call control routine 220, the microphone 222, the speaker 224, the transceiver 210, and the antenna 212 may be conventional functional units of existing wireless telephones. These functional units enable a user to place and receive telephone calls in a conventional manner. For example, a user may place a telephone call by entering a telephone number using the keypad 216 and pressing a send key, also on the keypad 216. The keypad 21 6 may be a conventional wireless telephone keypad, including the digits '0' through '9', the symbols '*' and '#', and 'SEND' and 'END' keys. The wireless telephone 102A may have additional keys or buttons in different locations from a conventional keypad, such as on a side of the telephone or in another area on the front of the telephone. Such additional keys or buttons are considered part of the keypad 216 for the present description. The wireless telephone 102A may also have a touch screen display or other input means, that will also be considered part of the keypad 216. The user interface 214 communicates the user's actions to the call control routine 220, along with displaying information to the user via the display 218. The call control unit 220 places the call using the transceiver 210 and the antenna 212 in a conventional manner. The user may then engage in the telephone conversation in a conventional manner using the microphone 222 and the speaker 224. The WAP protocol stack 208 preferably conforms to the standards set by the WAP Forum, and gives the wireless telephone 102A data communication capabilities. WAP protocol stacks 208, suitable for the present invention, are currently available.

The data application 204 may be, for example, a PIM, providing various applications or functions, such as a contact list, a to-do list, a calendar, and a memo pad, such as a version of the PIM that operates in the StarTAC® clipOn Organizer device. Thus, the wireless telephone 102A may be a "smart phone" (i.e., a wireless telephone with built-in PIM capabilities). The dataset 202 preferably contains user data entered via the data application 204. For example, if the data application 204 is a PIM, then the dataset 202 would contain the user's contacts, to-do items, calendar entries, and memos. The present invention, however, can synchronize any type of data, not just PIM data. In the preferred embodiment of the present invention, the dataset 202 also contains synchronization information, as will be described below.

Just as the wireless device 102 may be any of a wide variety of wireless devices, the data application 204 may also be any of a wide variety of data applications. For example, if the wireless device 102 is a notebook computer connected to a wireless telephone (or incorporating a wireless interface), then the data application 204 may be an ordinary PC PIM application, such as Sidekick® or Microsoft®, Outlook®, running on the notebook computer. Alternatively, if the wireless device 102 is a PDA with wireless capabilities, such as a Palm organizer, then the data application 204 may be a PIM running on the PDA. Also, as described above, the data application 204 may be any of a wide variety of applications involving any other type of data. Thus, the data application 204 may be virtually any application involving any type of data running on any device that has wireless communication capabilities.

In the preferred embodiment, the wireless device 102 is a wireless telephone, and the data application 204 is a PIM application. Thus, the wireless device 102 is a smart phone 102A in the preferred embodiment. A user may use the smart phone 102A in a conventional manner for existing smart phones. For example, a user may use the PIM application 204 to enter contact information, such as a person's name, telephone number, and address. The user may enter an entire list of contacts, comprising contact information for a number of different people. The PIM application 204 will store this data into the dataset 202, through the sync client 206. The user may then use the PIM application 204 to select the telephone number of a person in the contact list and cause the wireless telephone 102A to dial the selected telephone number. The data application 204 passes the selected telephone number to the call control unit 220 and the call control unit 220 places the call.

In the preferred embodiment, the data application 204, the sync client 206, the WAP protocol stack 208, the user interface 214, and the call control unit 220 comprise software routines or applications residing in the memory of the wireless telephone 102A and running on a programmable microprocessor of the wireless telephone 102A. The dataset 202 is also preferably stored in the memory of the wireless telephone 102A. In one embodiment of the present invention, all of these software routines are stored in the same memory and run on the same microprocessor within the wireless telephone 102A, while, in another embodiment, the dataset 202, the data application 204 and the sync client 206 are stored in a different memory from the other routines and the data application 204 and the sync client 206 run on a different microprocessor from the other routines. In the case of using two separate memories and microprocessors, the WAP protocol stack 208 may be stored in either memory and may run on either microprocessor. As another alternative, there may be a single memory that is shared by two separate microprocessors, so that all data and software are stored in the single memory, but some routines run on one microprocessor, while others run on the other microprocessor.

Figure 3:
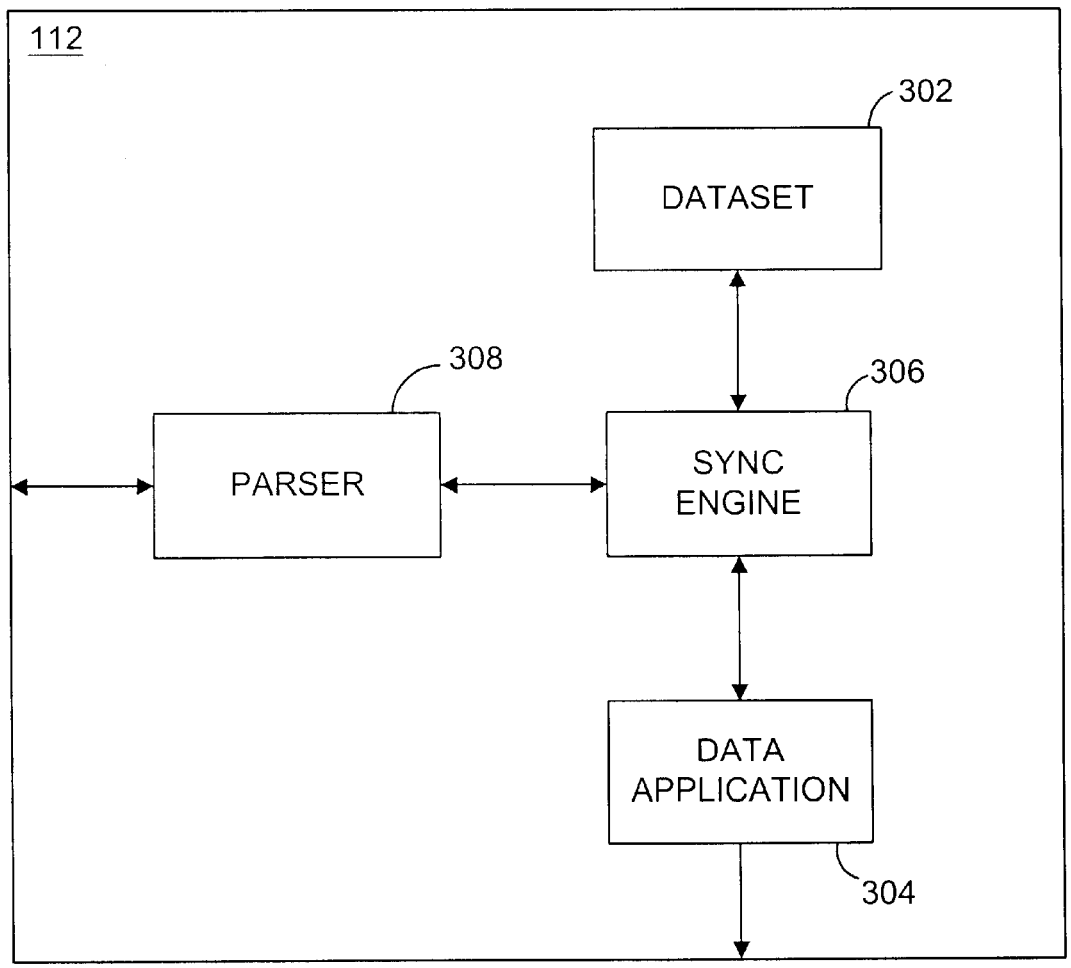
FIG. 3 is a functional block diagram of a sync server that may be used in the preferred embodiment of the present invention.

FIG. 3 is a functional block diagram of the sync server 112. The sync server 112 preferably comprises a dataset 302, a data application 304, a sync engine 306, and a parser 308. The parser 308 may receive data from the wireless device 102 in various content formats and using different protocols, depending on the content formats and protocols used by the wireless device 102 and the functionality of the format gateway 110 and the protocol gateway 106. The wireless device 102 preferably uses a proprietary data content format of the sync engine 306, along with the WML format. The wireless device 102 also preferably uses the WTP protocol.

The data could be sent directly to the parser 308 without converting from either the WTP protocol or the WML format. Alternatively, either the protocol gateway 106 or the format gateway 110 may convert from the WTP protocol to the HTTP protocol and/or from the WML format to the HTML format. Thus, the parser 308 may receive data from the wireless device 102 in the proprietary format of the sync engine 306 or in the WML or HTML formats, using the WTP or HTTP protocols. Regardless of the format and protocol of the data received by the parser 308, the parser 308 strips out protocol information from the received data and converts the data, if necessary, into a format that is understood by the sync engine 306. In the preferred embodiment, the sync engine 306 uses a proprietary data content format. More specifically, in the preferred embodiment, the sync engine 306 uses "action objects," which are described below and in the incorporated references. In communications from the sync engine 306 to the wireless device 102, data conversions will be done in a converse manner.

The data application 304 may be a PIM application such as the server application located at the Internet site True-Sync.com. The dataset 302 preferably contains the user data of the PIM application 304. For example, the dataset 302 may contain a user's contact list, to-do items, calendar entries, and memos. In the preferred embodiment, the dataset 302 also contains information related to the synchronization of the wireless device 102 and possibly one or more other devices. Again, the present invention can synchronize any type of data, not just PIM data, so the data application 304 may be any type of application, involving any type of data.

A user may use the PIM application 304 in a conventional manner. The PIM application 304 uses Internet protocols and content formats, so that a user may gain access to the PIM application 304 using the Internet client 118 in a conventional manner. More specifically, a user would enter the URL for an Internet-based PIM application 304, such as TrueSync.com, into a web browser of the Internet client 118. When the Internet client 118 makes contact with the PIM application 304, which would typically be running on a server at a remote location, the PIM application 304 may send information requesting that the user log on to the PIM application 304. After the user has logged on to the PIM application 304, the user may use the PIM functions of the PIM application 304 in a conventional manner. For example, the user may use the PIM application 304 to enter a contact list, comprising the name, address, and telephone numbers for a number of different people or businesses. The PIM application 304 stores the user data in the dataset 302 through the sync engine 306. The data application 304 communicates with the sync engine 306 according to the formats required by the sync engine 306. In the preferred embodiment, the data application 304 communicates with the sync engine 306 using action objects, which are described below and in the incorporated references. In the preferred embodiment, the dataset 302 comprises an Oracle® database, and the sync engine 306 communicates with the dataset 302 using standard Java database connectivity (JDBC).

A user may also be able to access the data in the dataset 302 using the wireless device 102. This access would not involve the dataset 202. The wireless device 102 may comprise a WAP browser, such as an existing WAP browser. The WAP browser may send and receive data in WAP content formats, such as WML and WMLScript, using the WAP protocol stack 208. In one embodiment of the present invention, the WAP browser may send data to, and receive data from, the sync engine 306, through the parser 308. Thus, for example, data from the dataset 302 may be sent from the sync engine 306, through the parser 308, to the WAP browser, and displayed on the display 218 of the wireless device 102. For example, if the dataset 302 contains PIM data, then the user may use the WAP browser of the wireless device 102 to browse contact information stored in the dataset 302 to find a person's telephone number. The wireless device 102 may then be able to dial the telephone number to place a call to that person. The interface between the WAP browser and the dataset 302 may be a read-only interface, or the user may also be able to change data or store new data in the dataset 302. In another embodiment, the WAP browser may communicate with the data application 304, in a manner that is similar to the interface between the data application 304 and the Internet client 118, except that the WAP browser may use the WAP data content formats and protocols. Protocol and format conversion functions may be provided between the WAP browser and the data application 304, or the data application 304 may be configured to use WAP protocols and formats, in addition to the Internet protocols and formats.

The preferred embodiment of the present invention is described in connection with a conventional wireless network 104 and the Internet 108. However, the invention can be implemented in a wide variety of other wireless communication environments. For example, the wireless device 102 may be a telephone handset 102 that interfaces with a home PC via a cordless communication link. The home PC may operate as a cordless telephone base station, providing an interface between the cordless telephone handset 102 and the PSTN. The home PC may also function as the sync server 112. Further, the telephone handset 102 may implement a PIM application 204, and the home PC 112 may implement a PIM application 304. As another alternative, the wireless device 102 may be a wireless PDA, the sync server 112 may be a home PC, and the wireless interface 130 between the wireless device 102 and the sync server 112 may be an infrared interface, an RF interface, or an interface based on Motorola's BlueTooth technology.

Regardless of the communication environment in which the present invention is implemented, the present invention preferably comprises a first data application 204, a first dataset 202, and a sync client 206 in a wireless device 102 and a second data application 304, a second dataset 302, and a sync engine 306 in a sync server 112, where the wireless device 102 communicates with the sync server 112 over some form wireless communication channel or interface. A user may enter various data into the first dataset 202 and various other data into the second dataset 302. The user may then want to synchronize these two sets of data, so that both datasets 202 and 302 contain the same data. The synchronization methods of the present invention will effectively synchronize the datasets 202 and 302, for various communication environments, including various wireless communication environments.

In the synchronization methods of the present invention, the sync client 206 preferably stores information in the dataset 202 that enables the sync client 206 to determine which changes to the dataset 202 should be sent to the sync engine 306 to synchronize the dataset 202 with the dataset 302. The sync engine 306 also preferably stores information in the dataset 302 that enables the sync engine 306 to determine which changes to the dataset 302 should be sent to the sync client 206 to synchronize the dataset 202 with the dataset 302. In addition, the sync client 206 preferably stores additional data in the dataset 202, and the sync engine 306 preferably stores additional data in the dataset 302, to enable the sync engine 306 to perform Conflict resolution and duplicate resolution functions between the changes made to the dataset 202 and the dataset 302. This additional change resolution data that is stored in the dataset 202 will be transmitted from the sync client 206 to the sync engine 306 during synchronization.

As an example, in the preferred embodiment, a user may enter a first set of PIM data, such as a new contact entry, into the PIM application 204 using the keypad 216 and the user interface 214. The data application 204 communicates the first set of PIM data to the sync client 206. The sync client 206 stores the first set of PIM data in the dataset 202, along with related synchronization information, such as a timestamp indicating the time at which the user entered each item of the first set of PIM data and an indication that each item of the first set of PIM data represents a fresh change relative to the dataset 302 (i.e., a change that, to the knowledge of the sync client 206, has not been synchronized to the dataset 302). Generally, the sync client 206 stores information in the dataset 202 to indicate which data in the dataset 202 have been changed since the last time the dataset 202 was synchronized with the dataset 302.

In addition to receiving changes to the dataset 202 directly from a user of the wireless device 102, the sync client 206 may also receive changes from other sync servers during synchronizations with those other sync servers. Generally, the sync client 206 will mark changes received from other sync servers as fresh relative to the dataset 302. However, during a possible synchronization with another sync server, the other sync server may send information to the sync client 206 indicating that specific data from the other sync server has already been synchronized to the dataset 302. In this case, the sync client 206 will not mark the specified data as fresh relative to the dataset 302. When the dataset 202 is synchronized with the dataset 302, the sync client 206 will send to the sync engine 306 those changes to the dataset 202 that have been marked as fresh changes relative to the dataset 302.

The other sync server will also preferably send information to the sync client 206 indicating the time at which changes were initially made, at whichever device the changes were made. Thus, if the user initially made a change at another device and if another sync server found out about that change through a synchronization with that other device, then, when the other sync server sends the change to the sync client 206 during a subsequent synchronization, the other sync server will also send a timestamp to the sync client 206 indicating the time at which the change was made it the other device. The sync client 206 will store this information in the dataset 202, along with the change. If a change is made by a user to the dataset 202 at the wireless device 102, using the data application 204, the sync client 206 stores the changed data into the dataset 202, along with a timestamp from the sync client 206 that indicates the time at which the data was changed by the user. During a subsequent synchronization with the sync engine 306, the sync client 206 will send all changes that it has marked as fresh relative to the dataset 302, along with the timestamps that indicate the time at which the chances were initially made, in whichever devices the changes were initially made. In the description below, the phrase "fresh changes" shall include data value changes and synchronization information, such as timestamps indicating the time at which the changes were initially made. The phrase "fresh changes" shall also generally include a record ID number to identify the specific data record to which the change was made.

The user may also enter a second set of PIM data into the PIM application 304 using the Internet client 118. The data application 304 communicates the second set of PIM data to the sync engine 306. The sync engine 306 stores the second set of PIM data in the dataset 302, along with related synchronization information, such as timestamps indicating the time at which the user entered the second set of PIM data and an indication that the set of PIM data represents a fresh change. In the preferred embodiment, the sync server 112 stores enough synchronization information in the dataset 302 to determine which particular data need to be sent to each other's dataset to synchronize the particular dataset with the dataset 302. Again, this synchronization information will preferably include a timestamp indicating the time at which a particular change was initially entered into whichever device initially received the change. For example, the sync server 112 stores enough synchronization information to determine which data need to be sent to the sync client 206 to fully synchronize the dataset 202 with the dataset 302. In the preferred embodiment, the sync engine 306 also preferably stores and/or receives enough data to determine the relative sequence in which multiple changes were made to a common data record. In other words, if a first change was made to a specific data record in a first device at a first time, and a second change was made to the same data record in a second device at a second time, the sync engine 306 will preferably be able to determine which of the first and second changes was made more recently. Determinations regarding the sequence in which multiple changes were made to a common data record are used for conflict and duplicate resolution.

The information that is stored by the sync client 206 and the sync engine 306, along with techniques for conflict and duplicate resolution, are described in greater detail, for example, in the incorporated U.S. patent applications having Ser. No. 09/136,215, U.S. Pat. No. 6,295,541 Ser. No. 09/208,815 U.S. Pat. No. 6,477,545, and Ser. No. 09/311, 781, U.S. Pat No. 6,487,560.

In one embodiment of the present invention, the keypad 216 of the wireless telephone 102A comprises a synchronization key. A user may press the synchronization key to activate a function of the present invention to synchronize the dataset 202 with the dataset 302. When a user presses the synchronization key, the user interface 214 detects the activation of this key and informs the data application 204 of the key's activation. In response, the data application 204 activates the sync client 206 to perform the synchronization. In other embodiments of the present invention, a synchronization may be initiated by various other events, such as a user entering new data into either the dataset 202 or the dataset 302, or the occurrence of a timer event, such as a preset time of day being reached.

The sync client 206 and the sync engine 306 communicate with each other to synchronize the datasets 202 and 302, using one or more of the synchronization methods of the present invention. The synchronization methods of the present invention include technology that is described, for example, in the incorporated U.S. patent applications having Ser. No. 09/136,215 U.S. Pat. No. 6,275,541, Ser. No. 09/208,815 U.S. Pat. No. 6,477,545, and Ser. No. 09/311, 781 U.S. Pat. No 6,487,560.

For the purpose of the present invention, it is important to understand that the sync server 112 is capable of performing partial, or incremental synchronization services. The sync server 112, using its action object protocol, can accept fresh changes from the dataset 202 and can also send fresh changes from the dataset 302 to the wireless device 102.

Fresh changes are changes made in one dataset (e.g. by the user) that are believed not to be known to the other dataset (i.e., that may need to be propagated to the other dataset). The wireless device 102 and the dataset 302 may each have sufficient intelligence to only accept the fresh changes that will not overwrite other, even newer local fresh changes, as described in the incorporated U.S. patent application having Ser. No. 09/311,781 U.S. Pat. No. 6,487,560 (filed May 13, 1999). In the preferred embodiment, all sending of changes may be performed free-form in either direction, at any time, in any order, in large batches or small, without harming data integrity. Due to latency effects or non-FIFO effects of wireless communications, suspect changes may be discarded without full acknowledgment, and thus they would eventually be re-sent again, hopefully with better acknowledgment. Eventually, when neither dataset has fresh records for the other, the datasets will be in a synchronized state. The extremely flexible underlying synchronization protocol (based on action objects) just summarized is the preferred underlying core synchronization logic of the present invention.

Figure 4:
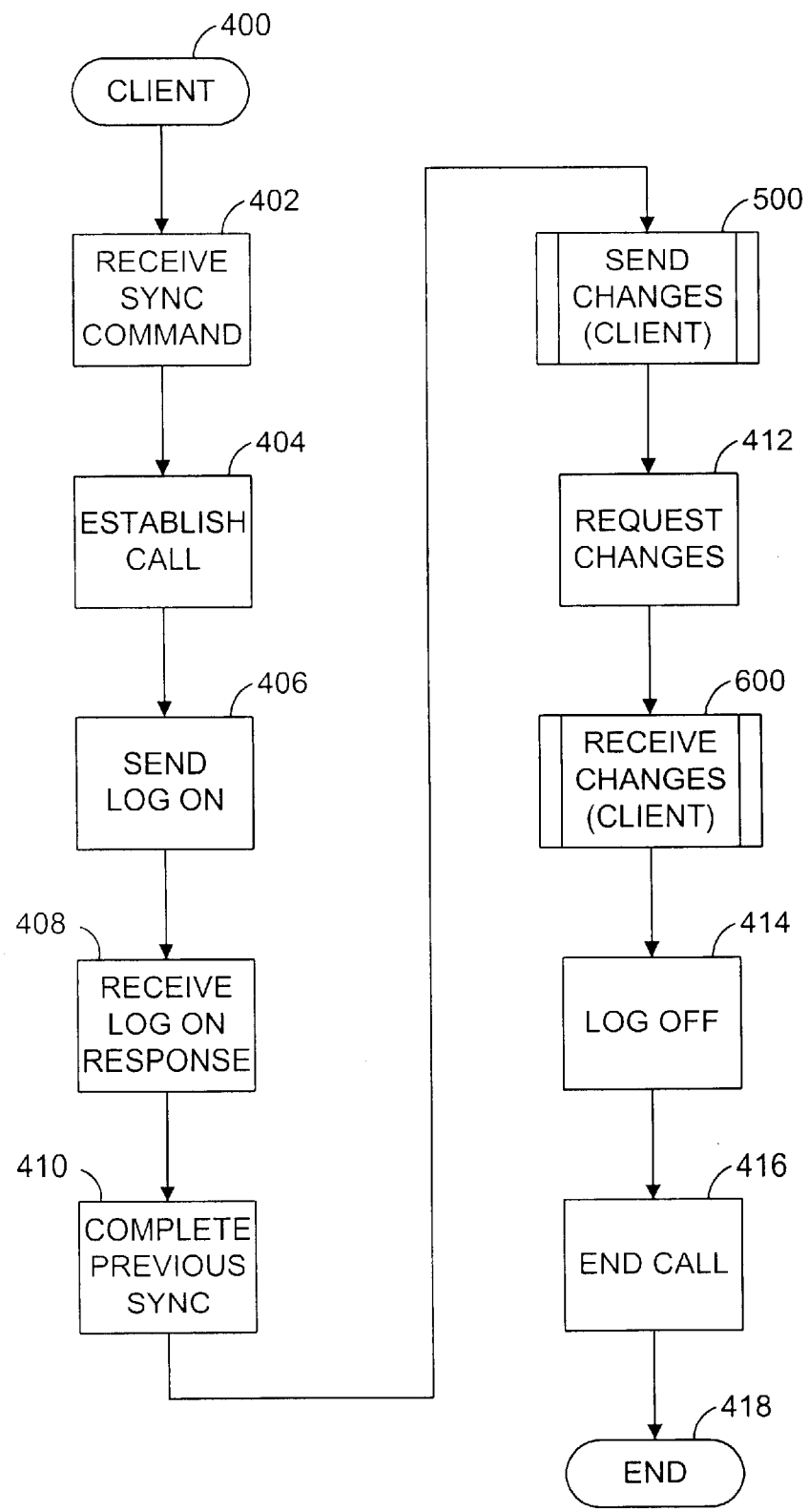
FIG. 4 is a flowchart illustrating a synchronization method of the present invention that may be performed by a wireless communication device.
Figure 7:
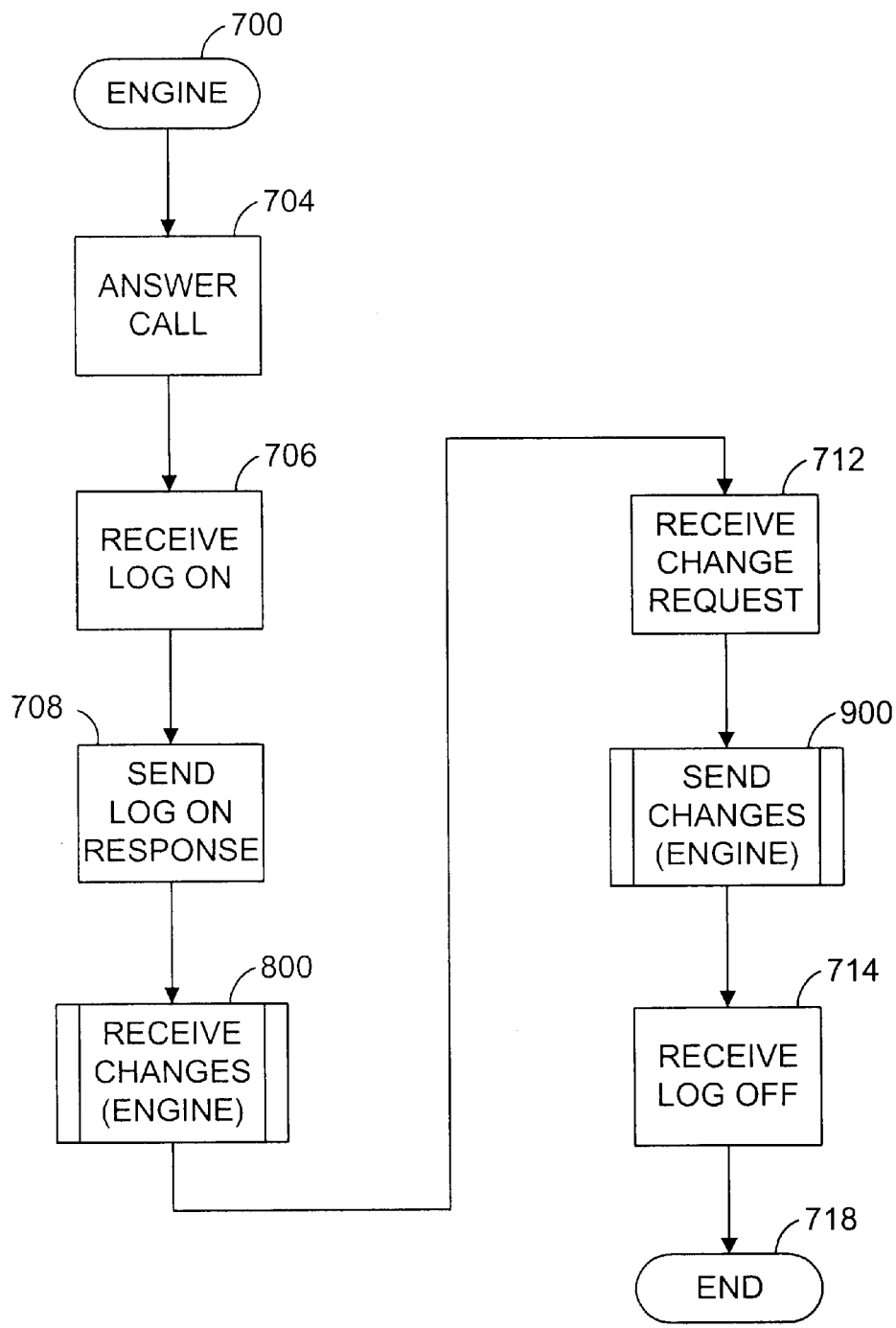
FIG. 7 is a flowchart illustrating a synchronization method of the present invention that may be performed by a sync server.

FIG. 4 is a flowchart illustrating a first synchronization method performed by the wireless telephone 102A to synchronize the datasets 202 and 302. FIG. 7 is a flow chart illustrating a corresponding and simultaneous synchronization method performed by the sync engine 306. The sync methods of FIGS. 4 and 7 perform bi-directional synchronizations. That is fresh chances are sent from the dataset 202 to the dataset 302 and from the dataset 302 to the dataset 202. These methods are the preferred synchronization methods of the present invention for a connection-oriented communication system, although these methods may be employed in any communication system.

The first method of the wireless telephone 102A begins at an initial step 400, while the first method of the sync engine 306 begins at an initial step 700. At a step 402, the user interface 214 of the wireless telephone 102A detects the user activation of the synchronization key of the keypad 216 and sends a sync command to the data application 204. In response, the data application 204 activates the sync client 206. Alternatively, the synchronization function may be initiated by the user in other manners, such as by allowing the user to select the sync function from a menu on the display 218 or by interpreting a spoken command from the user. Or, the synchronization function may be initiated automatically based on an occurrence of a preset condition, such as the time of day reaching a specified time.

Next, the sync client 206 performs a number of steps in an attempt to synchronize the dataset 202 with the dataset 302. If any of these steps fail, the sync client 206 may repeat the step until it is successful. At sonic point, if a step is still unsuccessful after a certain number of attempts, the sync client 206 may abort the synchronization process. The sync client 206 may automatically attempt the synchronization process again later, or it may not perform any further synchronization activities until the synchronization key is activated again. Similarly, the sync engine 306 also performs a number of steps in an attempt to synchronize the dataset 202 with the dataset 302. Again, if a step fails, the sync engine 306 may repeat a failed step until it is successful, or it may, at some point, abort the synchronization process.

At a step 404, the sync client 206 sends commands to the WAP protocol stack 208, causing the WAP protocol stack 208 to initiate a data call to the sync server 112. More specifically, the sync client 206 initiates a data call function of the WAP protocol stack 208, providing the data call function with the URL and port of the sync server 112. This will establish a connection-oriented communication channel between the wireless telephone 102A and the protocol gateway 106. The protocol gateway 106 establishes a connectionless. communication channel to the sync server 112, possibly through the format gateway 10. These communication channels will facilitate communications between the wireless telephone 102A and the sync serve 112, until the data call is terminated. The WAP protocol stack 208 uses the transceiver 210 and the antenna 212 to communicate with the wireless network 104, and through the wireless network 104 and the Internet 108 to the sync server 112. For subsequent steps, the sync client 206 communicates with the sync server 112 through the WAP protocol stack 208, the transceiver 210, the antenna 212, the wireless network 104, and the Internet 108. At a step 704, the sync server 112 detects and answers the incoming call from the sync client 206.

More specific to the preferred embodiment of the present invention, the sync client 206 and the sync engine 306 may communicate with each other using action objects. Action objects will be described in greater detail below and are described in still greater detail in the incorporated references. An action object is first sent to the WAP protocol stack 208. The WAP protocol stack 208 adds formatting and routing information according to the WAP specifications to create a WAP data packet. The WAP protocol stack 208 then transmits the data packet to the wireless network 104, over the wireless interface 130. The wireless network 104 routes the data packet to the protocol gateway 106, through the connection-oriented communication channel established for the data call. The protocol gateway 106 converts the data packet from the WAP protocol to the TCP/IP protocol of the Internet 108, and transmits the data packet to the Internet 108. The Internet 108 routes the data packet to the sync server 112. If the format gateway 110 is present in the communication system, then the data packet is first routed to the format gateway 110 before it is routed to the sync server 112. The format gateway 10 converts the data packet from WAP content formats to Internet content formats before passing the data packet on to the sync server 112. The parser 308 receives the data packet in WAP content format, in Internet content format, or directly in action object format. The data packet will also contain either WAP or Internet protocol information. The parser 308 strips out the original action object sent by the sync client 206, and forwards the received action object to the sync engine 306. Alternatively, if the sync client 206 sent the data in WML format, for example, then the parser 308 will convert the received WML or HTML format (depending on whether the format gateway 110 converted the data packet from WML to HTML) into an action object format. The sync engine 306 may also send action objects to the sync client 206 using a converse data transmission method.

At a step 406, the sync client 206 sends all action object to the sync engine 306, in the form of an Action Logon, along with some log on information. The concept of action objects and the function of various action objects was described, for example, in U.S. patent application Ser. No. 09/311,781. At a step 706, the sync engine 306 receives the Action Logon object and the log on information. The log on information may include, for example, a user name, a password, and a device identification number (ID). The ID may be, for example, a serial number of the wireless device 102A. The sync engine 306 allows the sync client 206 to log on to the sync engine 306 only if the log on information is valid.

After the step 406, the sync client 206 waits for an action object called an Action Logon Response from the sync server 112. If the sync client 206 does not receive an Action Logon Response object within a certain period of time, the sync client 206 may return to the step 406 and resend the Action Logon object. At a step 708, the sync engine 306 sends an Action Logon Response object to the wireless telephone 102A. The Action Logon Response object indicates whether the sync client 206 has successfully logged onto the sync server 112. At a step 408, the Action Logon Response object is received by the sync client 206. If the Action Logon Response object indicates that the attempted log on was not successful, then the sync client 206 may return to the step 406 and resend the Action Logon object. Otherwise, the sync client 206 advances to a step 410.

At the step 410, the sync client 206 determines whether a previous synchronization attempt remains uncompleted. A previous attempt may not have been completed, for example, if the sync client 206 abandoned the previous attempt after failing to complete a step of the sync method. If a previous attempt has not been completed, then the sync client 206 resumes the sync method for the previous attempt at the same point at which the previous failure occurred. Once the sync method has been completed for the previous attempt, the sync client 206 resumes the sync method for the present synchronization at a step 500. Depending on the point at which the previous sync attempt failed, the current sync attempt may be combined with the previous sync attempt, so that the method need not be executed twice. For example, if the previous sync attempt failed before any changes were sent by either the sync client 206 or the sync engine 306, then the sync method only needs to be performed once for all of the changes that would otherwise have been sent during the two separate sync attempts.

Figure 5:
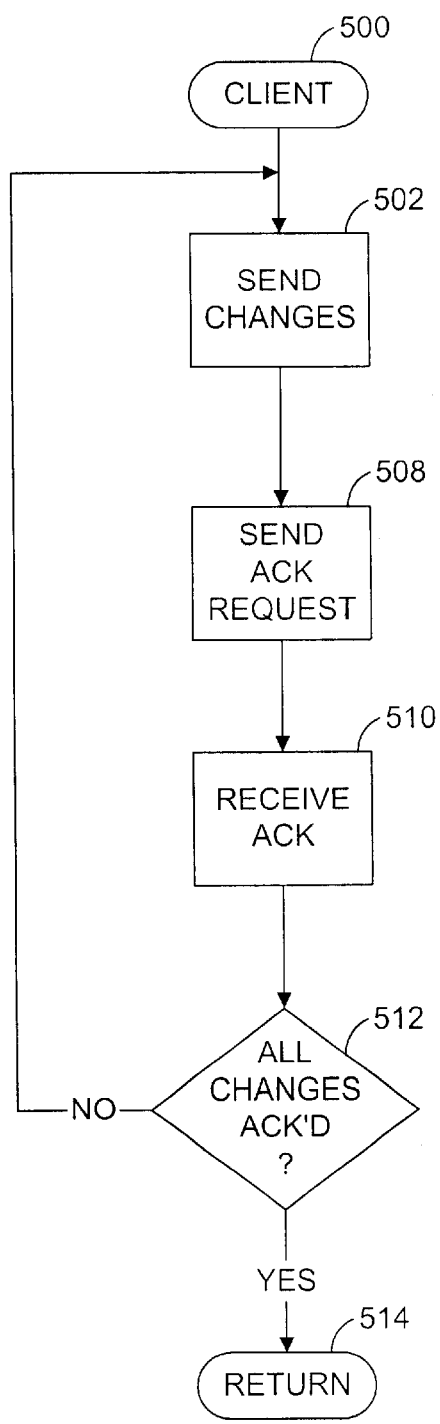
FIG. 5 is a flowchart illustrating a method for sending changes from a sync client to a sync server in a preferred embodiment of the present invention.

At a step 500, the sync client 206 performs a method for sending changes to the sync engine 306. Thus, for example, if a user used the data application 204 to change the telephone number of a person for whom data is stored in the dataset 202, then, at the step 500, the sync client 206 will send the new telephone number to the sync engine 306 for incorporation into the dataset 302. The method of step 500 is illustrated in FIG. 5. At a step 800, the sync engine 306 performs a method for receiving these changes from the sync client 206. As described in greater detail below and in the incorporated references, the method of the step 800 includes steps of reconciling the changes from the sync client 206 with other changes of which the sync engine 306 is aware, and storing changes that survive reconciliation in the dataset 302. The method of step 800 illustrated in FIG. 8. The methods of FIGS. 5 and 8 will be described below.

At a step 412, the sync client 206 sends an Action Retrieve Records object to the sync engine 306. The Action Retrieve Records object is received by the sync engine 306 at a step 712. The Action Retrieve Records object is a request from the sync client 206 for the sync engine 306 to send changes to the sync client 206. The sync client 206 may specify, in the Action Retrieve Records object, the number of changes that the sync engine 306 is to send to the sync client 206 during this synchronization. Alternatively, the sync client 206 may specify, in the Action Retrieve Records object, at maximum amount of data that should be sent by the sync engine 306 to the sync client 206 during this synchronization, so as to avoid the transmission of one or more large changes, such as a lengthy memo that has been entered at the sync server 112. The sync engine 306 may have received changes from the user through the data application 304 or from other sync servers or other sync clients through prior synchronizations. Preferably, the sync engine 306 receives the Action Retrieve Records object after it has completed conflict and duplicate resolution of the changes received at the step 800. Regardless of when it receives the Action Retrieve Records object, however, the sync engine 306 will preferably wait until it completes the conflict and duplicate resolution before it proceeds to a step 900 to send changes to the sync client 206. The sync engine 306 will only send changes that survived the conflict and duplicate resolution.

Figure 6:
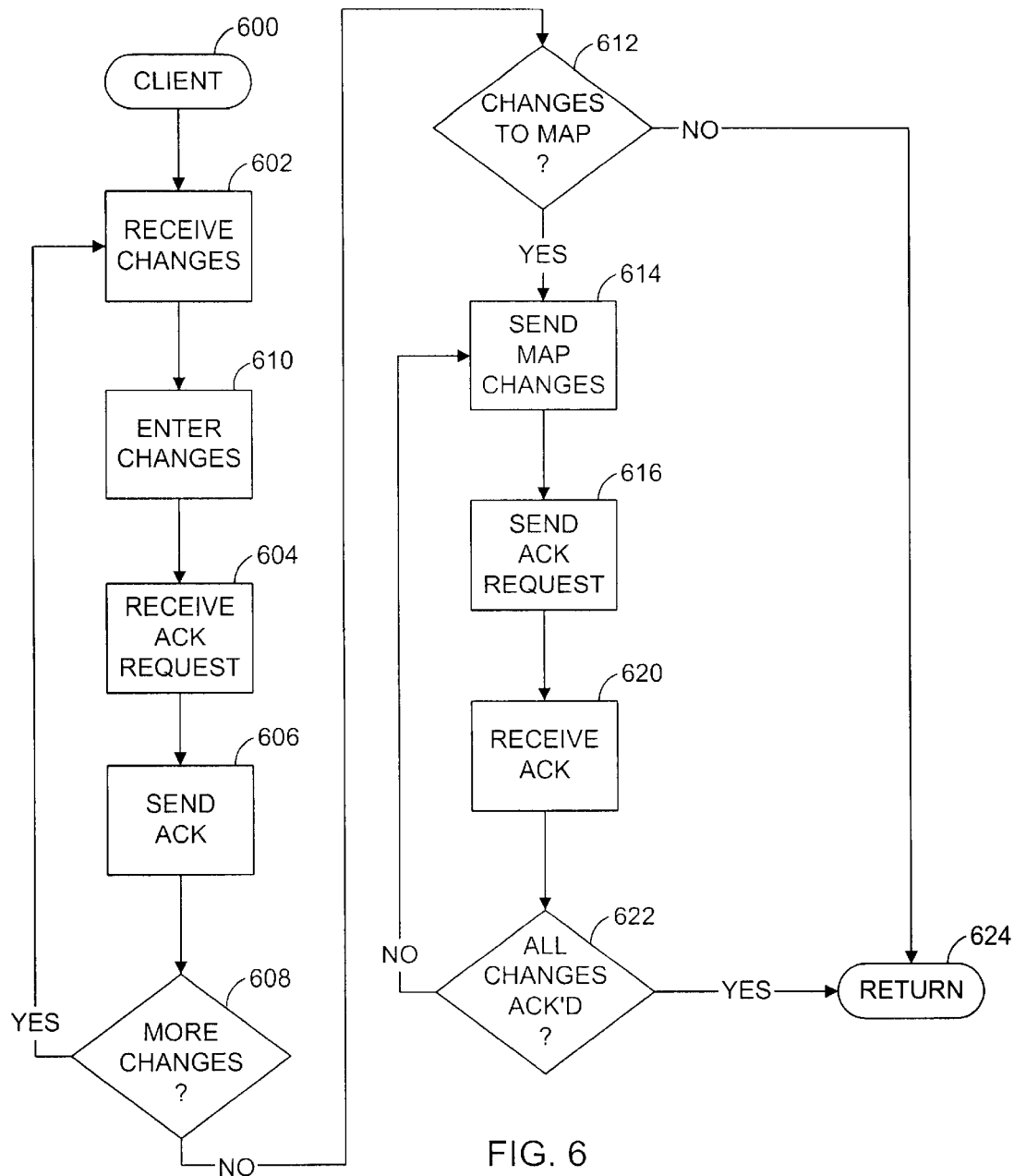
FIG. 6 is a flowchart illustrating a method for receiving changes at a sync client, sent by a sync server, in a preferred embodiment of the present invention.
Figure 9:
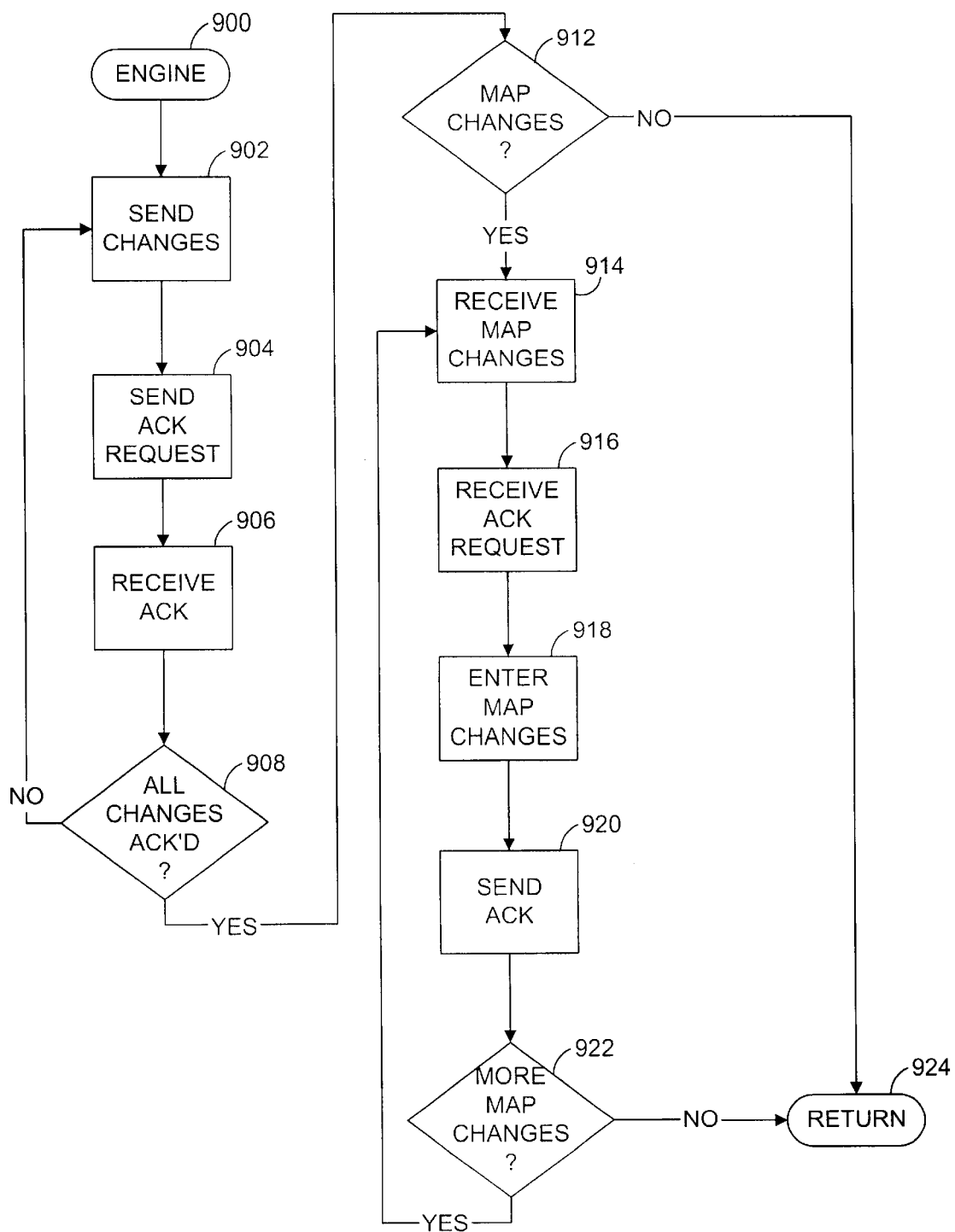
FIG. 9 is a flowchart illustrating a method for sending changes from a sync server to a sync client in a preferred embodiment of the present invention.

At the step 900, and in response to the Action Retrieve Records object, the sync engine 306 performs a method for sending chances to the sync client 206. This method is illustrated in FIG. 9. At a step 600, the sync client 206 performs a method for receiving these changes from the sync engine 306. This method is illustrated in FIG. 6. The methods of FIGS. 9 and 6 will be described below.

At a step 414, the sync client 206 sends an Action Logout object to the sync server 112. The sync engine 306 receives the Action Logout object at a step 714 and logs the sync client 206 out of the sync server 112. The sync client 206 proceeds to a step 416, at which it terminates the data call with the sync server 112. The method of the sync client 206 ends at a terminal step 418. The method of the sync engine 306 ends at a terminal step 718.

Figure 8:
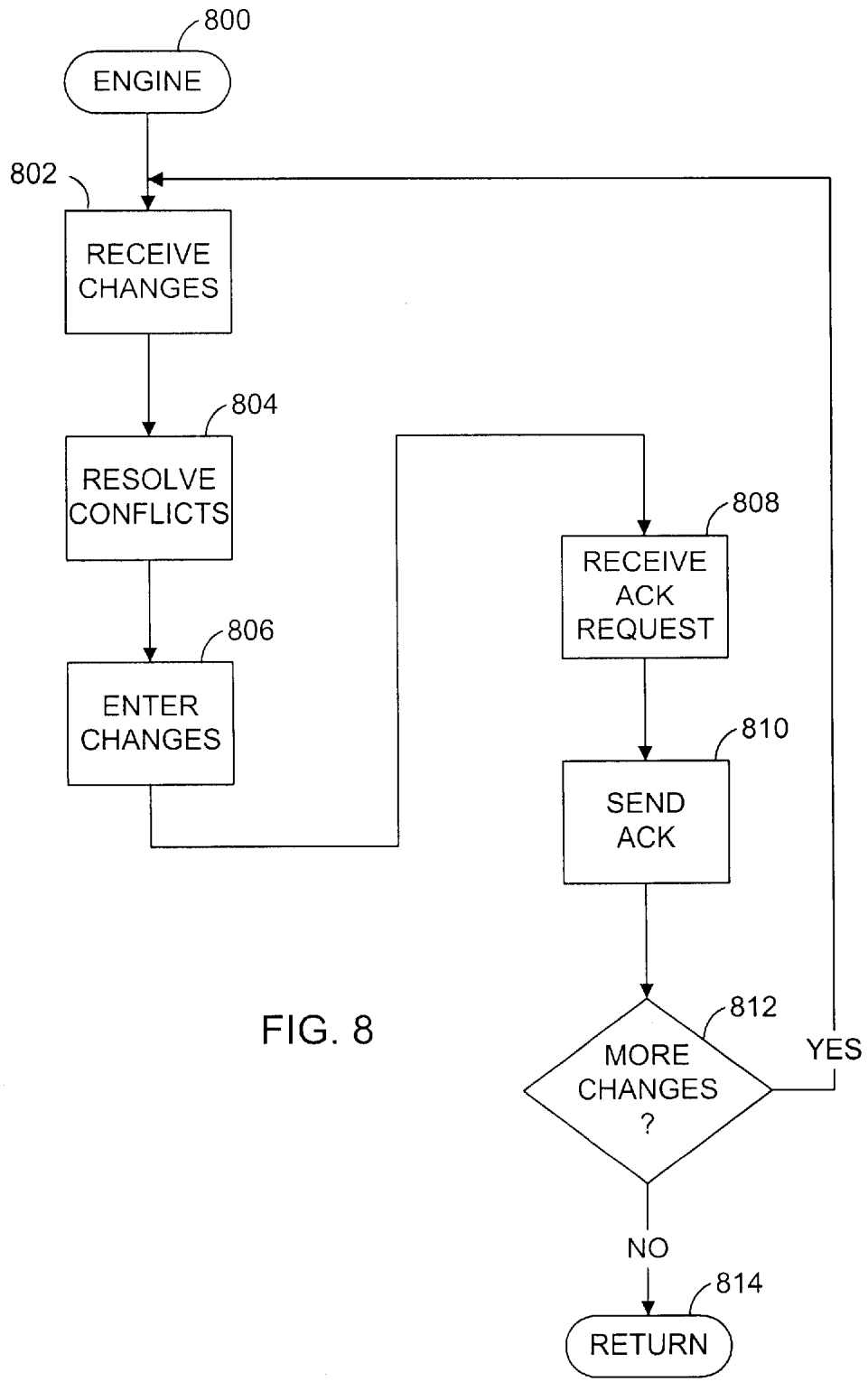
FIG. 8 is a flowchart illustrating a method for receiving changes at a sync server, sent by a sync client, in a preferred embodiment of the present invention.

Referring now to FIGS. 5 and 8, the method of the sync client 206 for sending changes to the sync engine 306 begins at an initial step 500, while the method of the sync engine 306 for receiving changes from the sync client 206 begins at an initial step 800.

At a step 502, the sync client 206 sends "fresh" changes to the sync server 112 in the form of action objects. The concept of fresh chances was described, for example, in U.S. patent application Ser. No. 09/136,215. The sync client 206 may send, for example, a number of Action Insert Record objects (for a newly-added record), Action Update Record objects (for a record that had already been entered, but where at least one value was changed), and Action Delete Record objects (for a record that was deleted). Each of these action objects will include, in addition to any new data values, the record ID of the sync client 206 for the specific record to be acted upon and a timestamp indicating the time at which the change was originally entered into a device. An Action Update Record object, for example, would include at least one new value for a specific record (for example, a new telephone number for a specific person), along with the record ID of the sync client 206 for the specific record and a timestamp indicating the time at which that new value was originally entered into a device. The sync client 206 may have received fresh changes from the user through the data application 204 or from other sync servers during prior synchronizations. The sync client 206 may initially send all of its fresh changes, or just a subset of its fresh changes. The changes are received at the sync engine 306 at a step 802.

At a step 804, the sync engine 306 performs conflict resolution and duplicate resolution between the received changes and any other changes of which the sync engine 306 is aware. Other changes may have been entered into the dataset 302 via the data application 304 or may have been sent to the sync engine 306 during synchronizations with other datasets. A conflict may arise, for example, when a user initially changes a certain item of a person's contact information, such as the persons home telephone number, to a first value in the dataset 302 using the data application 304 and subsequently changes the same item of the same person's contact information to a different value in the dataset 202 using the data application 204. In this case, the sync client 206 will send the different value from its dataset 202 to the sync engine 306 as a fresh change. The sync engine 306 will preferably determine that it also has a fresh change for the same item of the same person's contact information, and the conflict will be detected.

A duplicate situation may arise, for example, when a user first enters contact information for a certain person into the dataset 302 using the data application 304 and subsequently enters contact information for the same person into the dataset 202 using the data application 204, where contact information for that person was not previously in either dataset 202 or 302. Again, the sync client 206 will send its contact information for the person to the sync engine 306 as a flesh change, and tile sync engine 306 will detect the duplicate situation by determining that it also has new contact information for the same person.

In a conflict situation, the sync engine 306 will preferably determine which of the new, conflicting values was entered more recently by comparing the timestamp of the different value received from the sync client 206 with the timestamp of the first value stored in the dataset 302. If the change in the dataset 202 was made more recently than the change in the dataset 302, then the change from the dataset 202 will be overwritten into the dataset 302. More specifically, the first value for the item of the person's contact information will be replaced in the dataset 302 by the different value received from the sync client 206, and the timestamp for that item in the dataset 302 will be replaced with the timestamp received from the sync client 206. In addition, the corresponding change in the dataset 302 will then be marked as no longer being fresh relative to the sync client 206. In effect, the first change to the dataset 302 will have been discarded (by being overwritten and by being marked as not being fresh) and the change from the sync client 206 will have "survived" the conflict resolution. If, on the other hand, the value for the item stored in the dataset 302 were determined to have been entered more recently than the different value received from the sync client 206, then the change from the sync client 206 will be discarded, without entering the change into the dataset 302, and the first change to the dataset 302 will have survived the conflict resolution.

In a duplicate situation, the two sets of contact information for the same person are preferably merged into a single record. For example, if one set of contact information lists a business telephone number, but not a home telephone number, and the other set of contact information lists a home telephone number, but not a business telephone number, then the resulting record will include both the business telephone number from the one set of contact information and the home telephone number from the other set of contact information. A duplicate situation may also include a conflict situation where the same field of the contact information contains different values in the two sets. Such a conflict situation may be resolved in the same manner as for other conflict situations that do not also involve duplicate situations.

Techniques for resolving conflicts and duplicates are described in greater detail in the incorporated patent applications. For example, U.S. patent application Ser. No. 09/136,215 describes techniques for resolving various conflicts and duplicates that may arise under different scenarios, using various timestamps stored in the datasets 202 and 302, where the timestamps indicate the times at which different changes and synchronization events have occurred.

After resolving conflicts and duplicates related to the changes received from the sync client 206, the sync engine 306 enters those changes from the sync client 206 that survived the conflict and duplicate resolutions into the dataset 302 at a step 806. In the preferred embodiment, the steps 802, 804, and 806 will be performed as a loop, such that as each individual change is received from the sync client 206 at the step 802, a conflict and duplicate resolution is performed at the 804 step relative to that particular change, and, if the change survives the conflict and duplicate resolution, the change is entered into the dataset 302 at the step 806, before the next change is received from the sync client 206 at the step 802. A change from the sync client 206 may not survive a conflict resolution, for example, where the change was discarded as described above because a user also changed the same value in a different dataset, at a later time than the change to the dataset 202.

At a step 508, the sync client 206 sends an Action Request Ack Records object to the sync server 112. The sync engine 306 receives the Action Request Ack Records object at a step 808. In response, the sync engine 306 sends an Action Ack Records object at a step 810, listing the record ID of the sync client 206 for each change received at the step 802, as described in U.S. patent application Ser. No. 09/208,815. The sync client 206 receives the Action Ack Records object from the sync engine 306 at a step 510.

At a step 512, the sync client 206 compares the list of record IDs from the Action Ack Records object against its own list of record IDs for the changes it sent to the sync server 112 at the step 502. If the list of record IDs from the sync engine 306 does not include some of the record IDs from the list of record IDs of the sync client 206, then the sync client 206 returns to the step 502 to resend the changes that were not received by the sync engine 306. Alternatively, if the sync client 206 sent only a subset of its fresh changes in the previous step 502, then the sync client 206 also returns to the step 502 to send the remainder of its fresh changes, or another subset of fresh changes to the sync server 112. During the second pass through the step 502, the sync client 206 may send both changes that were missed by the sync server 112 during the first pass through the step 502 along with additional changes that have not yet been sent to the sync server 112. Thus, the steps 502, 508, 510, and 512 are executed as a loop until the sync client 206 has determined that all of its fresh changes have been received by the sync engine 306. If the list of record IDs received from the sync engine 306 matches the list of record IDs of the sync client 206, and if the sync client 206 sent all of its fresh changes to the sync server 112 during its previous pass through the step 502, then the sync client 206 proceeds to a terminal step 514. After the terminal step 514 of the method of FIG. 5, the sync client 206 returns to the method from which this method of FIG. 5 was called. For example, if the method of FIG. 5 was called or invoked at the step 500 after the step 410 of FIG. 4, then, after completion of the method of FIG. 5, the method of FIG. 4 will resume at the step 412.

Returning to the method of the sync engine 306, after the step 810, the sync engine 306 waits to receive further action objects from the sync client 206. After receiving the next action objects from the sync client 206, the sync engine 306 proceeds to a step 812. If the received action object is another change (i.e., an Action Insert Record object, an Action Update Record object, or an Action Delete Record object), the sync engine 306 returns to the step 802, otherwise, the sync engine 306 proceeds to a terminal step 814. After the terminal step 814 of the method of FIG. 8, the sync engine 306 returns to the method from which this method of FIG. 8 was called.

Referring now to FIGS. 9 and 6, the method of the sync engine 306 for sending changes to the sync client 206 begins at an initial step 900, while the method of the sync client 206 for receiving changes from the sync engine 306 begins at an initial step 600.

At a step 902, the sync engine 306 sends all, or a subset, of its fresh changes to the sync client 206. In the preferred embodiment, the sync client 206 may specify the number of changes that it wishes to receive when it sends the Action Retrieve Records object to the sync engine 306 at the step 412. Again, these changes may be Action insert Record objects, Action Update Record objects, and Action Delete Record objects. Please note, however, that one or more fresh changes may not have survived the conflict and duplicate resolutions of step 804 of the method of FIG. 8. Any change that does not survive the resolutions of step 804 is not sent to the sync client 206. The Action Update Record objects and the Action Delete Record objects will include, in addition to any new data values, the record ID of the sync client 206 for the specific record to be acted upon and a timestamp indicating the time at which the change was originally entered into a device. As described below, the sync engine 306 maintains a record ID mapping table that maps the record IDs of the sync client 206 to the record IDs of the sync engine 306, so that the sync engine 306 can send the sync client 206 the record IDs of the sync client 206. For an Action Insert Record object, however, the sync engine 306 will send its own record ID because the sync client 206 has not yet created the new record, and so a client record ID does not yet exist. The sync client 206 receives the changes from the sync engine 306 at a step 602.

At a step 610, the sync client 206 enters all the changes received at the step 602 into the dataset 202. The sync client 206 does not need to resolve conflicts or duplicates because the sync engine 306 resolved all conflicts and duplicates during the step 804 of the method of FIG. 8. However, in an alternative embodiment of the present invention, the wireless device 102 may have more processing capabilities, and may perform conflict and duplicate resolution, especially in situations where there are other sync servers and sync clients with which the wireless device 102 and/or the sync server 112 may synchronize its respective database.

At a step 904, after the sync engine 306 has sent all, or a subset, of its fresh changes to the sync client 206, the sync engine 306 sends an Action Request Ack Records object to the sync client 206, which is received by the sync client 206 at a step 604. In response, at the step 606, the sync client 206 sends an Action Ack Records object to the sync engine 306, which is received by the sync engine 306 at a step 906. The Action Ack Records object includes a list of record IDs for all changes received by the sync client 206 at the step 602, according to the record IDs of the sync client 206.

At a step 908, the sync engine 306 compares the list of record IDs from the Action Ack Records object against its own list of record IDs for the changes that it sent to the sync client 206 at the step 902. If the list of record IDs from the sync client 206 does not include some of the record IDs from the list of record IDs of the sync engine 306, then the sync engine 306 returns to the step 902 to resend the changes that were not received by the sync client 206. Alternatively, if the sync engine 306 sent only a subset of its fresh changes in the previous step 902, then the sync engine 306 also returns to the step 902 to send the remainder of its fresh changes, or another subset of fresh changes, to the sync client 206. During the second pass through the step 902, the sync engine 306 may send both changes that were missed by the sync client 206 during the first pass through the step 902 along with additional changes that have not yet been sent to the sync client 206. Thus, the steps 902, 904, 906, and 908 are executed as a loop until the sync engine 306 has determined that all of its fresh changes have been received by the sync client 206. If the list of record IDs received from the sync client 206 matches the list of record IDs of the sync engine 306, and if the sync engine 306 sent all of its fresh changes to the sync client 206 during its previous pass through the step 902, then the sync engine 306 proceeds to a step 912 and waits for further action objects from the sync client 206. At the step 912, if the sync engine 306 receives an Action Update Map object from the sync client 206, then the sync engine 306 proceeds to a step 914. Otherwise, the sync engine 306 proceeds to a terminal step 924.

Returning to the method of the sync client 206, after the step 606, the sync client 206 proceeds to a step 608 and waits for a period of time to receive further changes (i.e., Action Insert Record objects, Action Update Record objects, or Action Delete Record objects) from the sync engine 306. If the sync client receives further changes from the sync engine 306, the sync client 206 returns to the step 602. Otherwise, the sync client 206 proceeds to a step 612.

At the step 612, the sync client 206 determines whether the changes received at the step 602 included any Action Insert Record objects. If any such objects were received, then the sync engine 306 must update a record ID mapping table. This record ID mapping table was described in U.S. patent application Ser. No. 09/136,215 as a mapping table 1007. As described in that incorporated patent application, the mapping table 1007 maps record IDs of the sync engine 306 to record IDs of the sync client 206. So, if the changes received at the step 602 included any Action Insert Record objects, then the sync client 206 proceeds to a step 614. Otherwise, the sync client 206 proceeds to a terminal step 624.

When the sync engine 306 sends an Action Insert Record object, it includes its own record ID in the action object. When the sync client 206 receives an Action Insert Record object, the sync client 206 creates a new record, with a unique record ID in the dataset 202 and enters the information from the Action Insert Record object. At the step 614, the sync client 206 sends one or more Action Update Map objects to the sync engine 306, with a list of new client record IDs, along with corresponding engine record IDs, for each newly created record. The Action Update Map objects are received by the sync engine 306 at the step 914. At the step 614, the sync client 206 may send all, or a subset, of its map changes.

At a step 616, the sync client 206 sends all Action Request Ack Maps object to the sync server 112. The sync engine 306 receives the Action Request Ack Maps object at a step 916. At a step 918, the sync engine 306 updates its mapping table 1007 according to the record ID information contained in the Action Update Map objects. In response to the Action Request Ack Maps object received at the step 916, the sync engine 306 sends an Action Ack Maps object at a step 920, listing the record ID of the sync client 206 for each map change received at the step 914. The sync client 206 receives the Action Ack Maps object from the sync engine 306 at a step 620.

At a step 622, the sync client 206 compares the list of record IDs from the Action Ack Maps object against its own list of record IDs for the map changes it sent to the sync server 112 at the step 614. If the list of record IDs from the sync engine 306 does not include some of the record IDs from the list of record IDs of the sync client 206, then the sync client 206 returns to the step 614 to resend the chances that were not received by the sync engine 306. Alternatively, if the sync client 206 sent only a subset of its map changes in the previous step 614, then the sync client 206 also returns to the step 614 to send the remainder of its map changes, or another subset of map changes, to the sync server 112. During the second pass through the step 614, the sync client 206 may send both changes that were missed by the sync server 112 during the first pass through the step 614 along with additional changes that have not yet been sent to the sync server 112. Thus, the steps 614, 616, 620, and 622 are executed as a loop until the sync client 206 has determined that all of its map changes have been received by the sync engine 306. If the list of record IDs received from the sync engine 306 matches the list of record IDs of the sync client 206, and if the sync client 206 sent all of its map changes to the sync server 112 during its previous pass through the step 614, then the sync client 206 proceeds to the terminal step 624. At the terminal step 624, the sync client 206 returns to the method from which this method of FIG. 6 was called.

Returning to the method of the sync engine 306, after the step 920, the sync engine 306 proceeds to a step 922 and waits for a period of time to receive further action objects from the sync client 206. If the sync engine 306 receives another Action Update Map object, the sync engine 306 returns to the step 914, otherwise, the sync engine 306 proceeds to the terminal step 924. At the terminal step 924, the sync engine 306 returns to the method from which this method of FIG. 9 was called.

The preferred embodiment of the present invention includes other, more specific, features that improve the performance of the synchronization methods under the adverse conditions of a wireless environment and the limitations of many wireless devices. Some aspects of the preferred embodiment of the present invention relate to reducing the amount of data that must be transmitted over the wireless interface to achieve synchronization. First, at least some dataset labels that would otherwise be transmitted along with action objects to communicate changes to a dataset are preferably replaced by a shorter index number, such as a single byte value. Thus, instead of transmitting a label "Last Name" to indicate that the following string data is a person's last name, the preferred embodiment involves transmitting a byte value of negative one, followed by the actual string data representing the person's last name. Similarly, a byte value of negative two is transmitted instead of a label "First Name", and so on. Second, the preferred embodiment of the present invention utilizes the Unicode Transformation Format, Version 8 (UTF-8) to translate commonly used two-byte Unicode characters into single-byte characters. UTF-8 is a transformation format of ISO 10646 and is described in RFC 2279, the disclosure of which is hereby incorporated by reference. A copy of this document may be found on the world wide web at the site cis.ohio-state.edu/htbin/rfc/rfc2279.html. Characters are preferably stored as Unicode characters, but they are translated into UTF-8 characters before they are transmitted over the wireless interface.

Another aspect of the preferred embodiment relates to security issues of wireless interfaces. The WAP protocol stack 208 of the wireless device 102A preferably comprises a security layer, such as a Wireless Transport Layer Security (WTLS) layer. For a description of WAP, see e.g., Mann, S., *The Wireless Application Protocol*, Dr. Dobb's Journal, pp. 56–66, October 1999, the disclosure of which is hereby incorporated by reference.

Other aspects of the preferred embodiment relate to the latency found in most wireless systems and to the problems of lost messages and messages that are received in a different order than they were sent. Each data packet that is transmitted across the wireless interface contains sufficient header information so that the packet is self-defining. The recipient of the data packet can read the header information and determine the nature of the data packet and all appropriate responsive action without reference to any other data packet. For example, for the transmission of a fresh change, a data packet would preferably include all required dataset labels (or index numbers) all required data values, a record ID, a timestamp and an indication of the type of change involved. If it is necessary to break an action object into multiple parts, information is also included identifying the total length of the action object and, for each part, the placement of the part within the entire action object. In one embodiment, different techniques are utilized by the wireless device 102 and the sync server 112 to track reception of the multiple parts of an action object. When the wireless device 102 sends a multipart action object, it sends a part, requests an acknowledgment for that part and only continues onto the next part when it receives an acknowledge for the previous part. When the sync server 112 sends a multipart action object, it sends all parts and requests a single acknowledgment. The wireless device 102 builds a container for the action object based on the information related to the total length of the action object. As the wireless device 102 receives parts of the action object, it places these parts into the container, based on the indication of the placement of the part within the action object. When the wireless device 102 receives a request for acknowledgement from the sync server 112, the wireless device 102 can determine whether all of the parts of the action object were received by determining whether the container is full. If the wireless device 102 has not received all of the parts of the action object, it will not acknowledge receipt of the action object and will, instead, request that the action object be sent again. In another embodiment of the present invention, action objects can specify different parts of a multipart action object. In this embodiment, each part of a multipart action object will indicate which of the multiple parts it is. A sender of a multipart action object will send all parts and then send a single acknowledgment request. The recipient of the multipart action object will keep track of which parts it has received, based on the indications in each of the parts. The recipient will send an acknowledgment as long as it receives at least one part and it will indicate in the acknowledgment which of the parts it has received.

Another aspect of the preferred embodiment relates to the limited processing capability of most wireless devices and the latency of wireless systems. Suppose a sync server 112 sends an action object to a wireless device 102 and requests an acknowledgment. Suppose, however, that this transmission is delayed for some reason. After some time, the sync server 112 may resend the action object, assuming that the first action object was lost. Suppose further that the wireless device 102 eventually receives the first transmission of the action object. If the action object is a change, for example, the wireless device 102 will enter the change into its dataset 202, along with the timestamp from the action object. Suppose further that the wireless device 102 subsequently receives the second transmission of the action object. In the preferred embodiment, the wireless device 102 discards this second transmission of the action object as being a duplicate of a previously entered change. Specifically, the wireless device 102 checks the record ID of the second transmission of the action object and compares the timestamp stored in the dataset 202 that corresponds to that record ID against the timestamp in the second transmission of the action object.

The wireless device 102 only enters the change if the timestamp of the received action object is more recent than the corresponding timestamp stored in the dataset 202. In the case of duplicate transmissions of the same action object, the timestamps for the two copies of the action object will be the same, and the wireless device 102 will discard the action object that is received second. Discarding duplicate action objects conserves processing resources of the wireless device 102. In a similar manner, the sync server 112 will also discard a duplicate action object if the same situation arises in the opposite direction.

Another aspect of the preferred embodiment relates to the limited storage capacity of most wireless devices. Before a wireless device 102 can send changes to a sync server 112 during a synchronization method, the wireless device 102 must first create the action objects for transmission. Typically, these action objects are stored in a random access memory (RAM) as they are created. After transmission of the action objects, the wireless device 102 requests acknowledgment of the action objects. When the wireless device 102 receives an acknowledgment of a transmitted action object, it deletes the action object from its memory, instead of maintaining the action object in memory for possible future use. Discarding acknowledged action objects in this manner frees up memory space for other uses. If necessary, the wireless device 102 can recreate the action objects that it has deleted by again evaluating the synchronization information stored in the dataset 202

Figure 10:
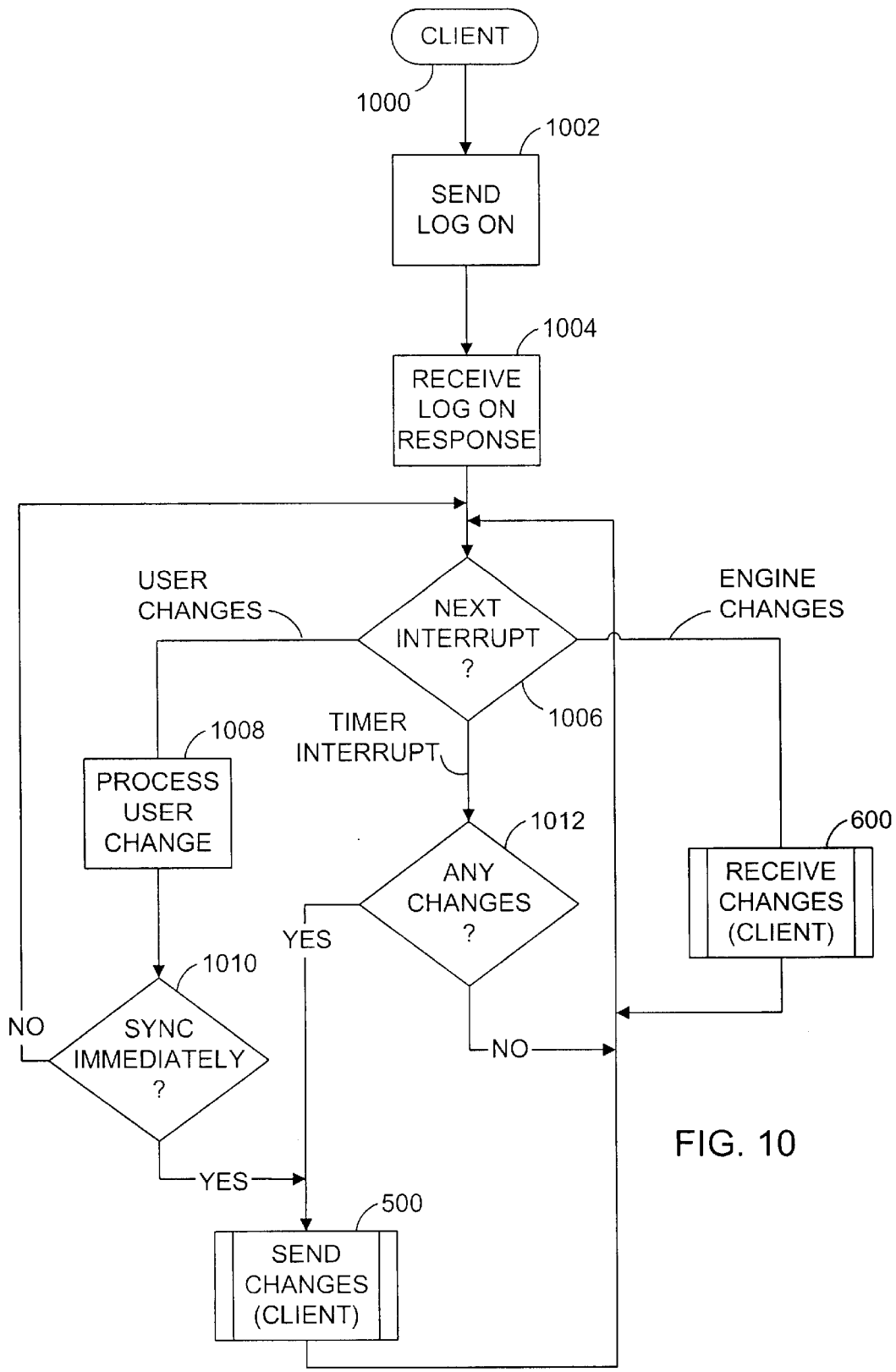
FIG. 10 is a flowchart illustrating another synchronization method of the present invention that may be performed by a wireless communication device.
Figure 11:
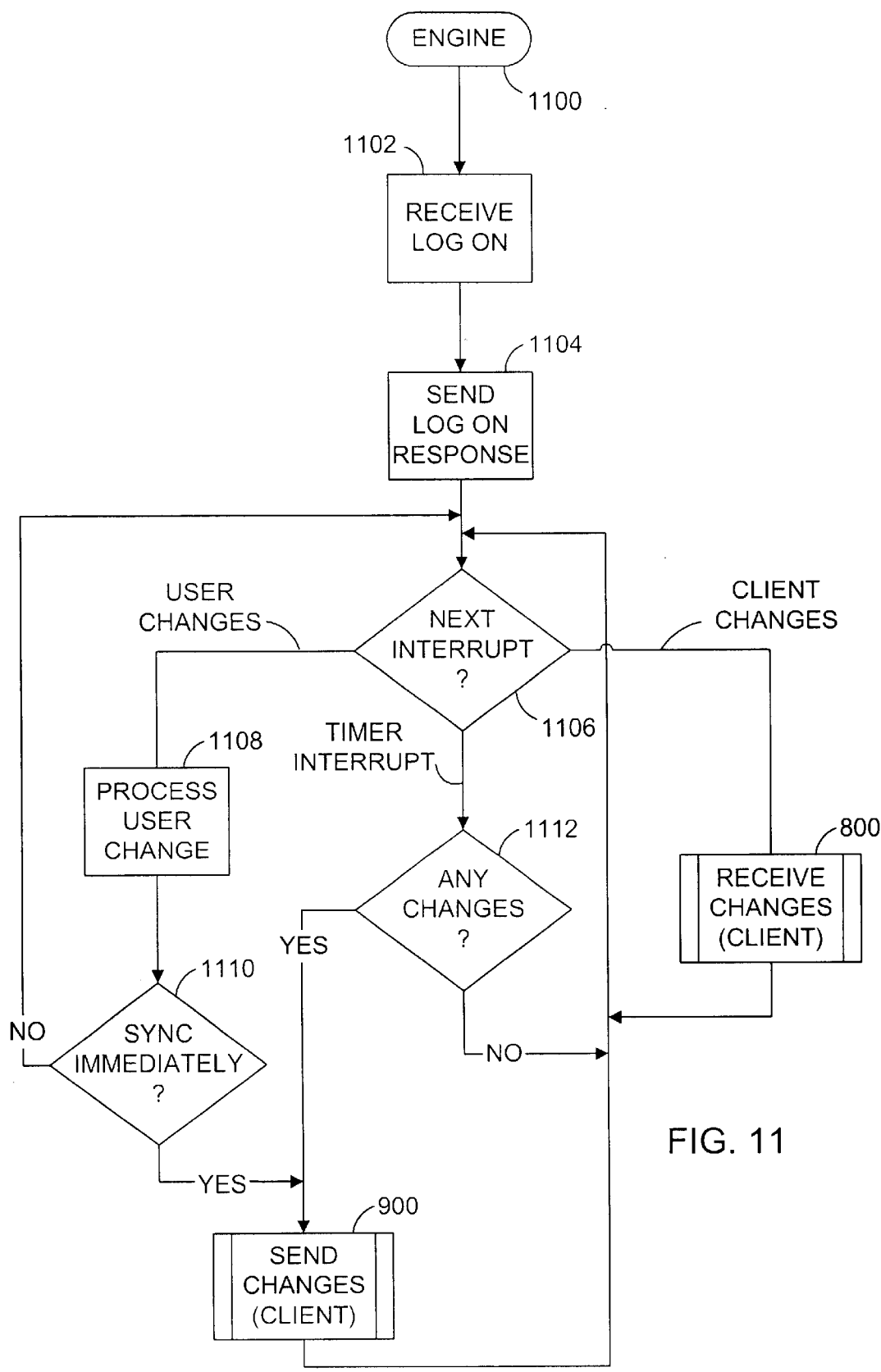
FIG. 11 is a flowchart illustrating another synchronization method of the present invention that may be performed by a sync server.

FIG. 10 is a flowchart illustrating a second synchronization method performed by the wireless telephone 102A to synchronize the datasets 202 and 302. FIG. 11 is a flow chart illustrating a corresponding and simultaneous synchronization method performed by the sync engine 306. The sync methods of FIGS. 10 and 11 are the preferred methods of the present invention for a connectionless communication system, although these methods may be employed in any communication system. The methods of FIGS. 10 and 11 will be particularly well suited for wireless data packet switching networks that are currently being developed, although the methods can also be used in other connectionless networks. In the new wireless data packet switching networks, there may be sufficient bandwidth that devices may synchronize with each other whenever desired, or under a wide variety of situations. Wireless service providers may charge for network usage based on the amount of data that is transmitted over the network, instead of based on the duration of a data call. Devices may be configured to initiate synchronizations at specific times of the day, at times when network traffic is relatively low, when a device has received one or more specific types of changes, when a device receives any changes at all, or under various other circumstances. In particular, a device may be configured to check it periodic intervals to determine if the device has any changes to be sent to another device and, if so, initiate a synchronization at that time.

The second method of the wireless telephone 102A begins at an initial step 1000, while the second method of the sync engine 306 begins at an initial step 1100. At a step 1002, the sync client 206 sends an Action Logon object to the sync engine 306, along with some log on information. The sync engine 306 receives the Action Logon object and the log on information at a step 1102. The log on information may include, for example, a user name, a password, and a device identification number (ID). The ID may be, for example, a serial number of the wireless device 102 A. The sync engine 306 determines whether the log on information is valid.

After the step 1002, the sync client 206 waits for an Action Logon Response object from the sync server 112. If the sync client 206 does not receive an Action Logon Response object within a certain period of time, the sync client 206 may return to the step 1002 and resend the Action Logon object. Similar to the methods of FIGS. 4 and 7, the sync client 206 and the sync engine 306 will each attempt to perform a number of steps during the methods of FIGS. 10 and 11. If an attempted step is not initially successful, the sync client 206 or the sync engine 306 may repeat the step until it is successful or, at some point, the sync client 206 or the sync engine 306 may abort the synchronization method. The sync engine 306 sends an Action Logon Response object indicating whether the attempted log on was successful, to the wireless telephone 102A at a step 1104. At a step 1004, the Action Logon Response object is received by the sync client 206. If the attempted log on was not successful, the sync client 206 may return to the step 1002 to resend the Action Logon object.

The steps 1002, 1004, 1102, and 1104 establish a communication session between the sync client 206 and the sync engine 306. These steps may be performed, for example, when the wireless telephone 102A is powered up. After the steps are performed, the sync client 206 proceeds to a step 1006 and the sync engine 306 proceeds to a step 1106. The remainder of the methods of FIGS. 10 and 11 may continue for an indefinite period of time. For example, the methods may continue for as long as the wireless telephone 102A remains powered up.

At the step 1006, the sync client 206 waits for a synchronization event to occur, such as a user change interrupt, a timer interrupt, or an engine change interrupt. A user change interrupt occurs when the user of the wireless telephone 102A enters a change into the database 202 using the data application 204, such as entering a new contact into the database 202. The data application 204 sends the user change to the sync client 206 in the form of a user change interrupt.

A timer interrupt occurs when a synchronization timer expires. In a connectionless communication system, synchronizations may be executed at any time by sending data packets between the sync client 206 and the sync engine 306, without establishing a data call. So, instead of requiring the user to manually in initiate a synchronization process, the sync client 206 and the sync engine 306 may automatically initiate synchronization processes at various pre programmed times. Also, a synchronization of data from the dataset 302 to the dataset 202 may occur at different times from synchronizations of data from the dataset 202 to the dataset 302. Thus, a user can simply enter changes into the dataset 202 using the data application 204 or into the dataset 302 using the data application 304, and the other dataset will automatically be updated during the next automatic synchronization. A timer may be used to determine when the next synchronization process should be initiated, where the timer would generate a timer interrupt at the appropriate times. The timer may be setup to initiate synchronization processes at specific times of the day, after specific time intervals have elapsed, or based on various other timing parameters. As another alternative, automatic synchronization processes may be initiated by either the sync client 206 or the sync engine 306 when it is determined that the wireless network 104 has a relatively lesser amount of traffic. The user may also manually initiate a synchronization process, for example, by pressing a synchronization key.

Another synchronization event that may occur is an engine change interrupt. An engine change interrupt indicates that the sync engine 306 has initiated a synchronization process. When the sync engine 306 initiates a synchronization process, it sends a data packet to the wireless telephone 102A. The data packet is received at the call control unit 220 of the wireless telephone 102A. When the call control unit 220 determines that the data packet is a synchronization data packet, it directs the data packet to the sync client 206. When the sync client 266 determines that the data packet contains changes from the sync engine 306, an engine change interrupt is detected.

At the step 1006, if the next interrupt is a user change, the method proceeds to a step 1008. If the next interrupt is a timer interrupt, the method proceeds to a step 1012. If the next interrupt is an engine change, the method proceeds to the step 600

At the step 1008, the sync client 206 enters the user change into the dataset 202, along with synchronization data, such as a timestamp and an indication that the user change is fresh. The method of FIG. 10 then proceeds to a step 1010. At the step 1010, the sync client 206 determines whether the user change should be immediately synchronized to the dataset 302. A user change may be immediately synchronized with the dataset 302 based on various preset criteria. For example, certain types of user changes, such as a calendar entry, may be automatically and immediately synchronized. The criteria upon which immediate synchronization occurs may be user configurable. If the current user change satisfies the criteria for immediate synchronization, then the method of FIG. 10 proceeds to the step 500. Otherwise, the sync client 206 returns to the step 1006. As described above, with reference to FIG. 5, the step 500 is a method for the sync client 206 to send changes to the sync engine 306. After the step 500, the sync client 206 returns to the step 1006.

If the next interrupt received by the sync client 206 is a timer interrupt, the sync client 206 advances to the step 1012. At the step 1012, the sync client 206 determines if there are any fresh changes to be sent to the sync engine 306. If there are fresh changes, the sync client 206 advances to the step 500 to perform the method of FIG. 5 for sending changes to the sync engine 306. After the step 500, the sync client 206 returns to the step 1006. Also, if there were no fresh changes at the step 1012, the sync client 206 returns to the step 1006.

If the next interrupt received by the sync client 206 is an engine change interrupt, the sync client 206 advances to the step 600 to perform the method of FIG. 6 to receive changes from the sync engine 306. After the step 600, the sync client 206 returns to the step 1006.

Returning to the method of FIG. 11, at the step, 1106, the sync engine 306 waits for a synchronization event to occur, such as a user change interrupt, a timer interrupt, or a client change interrupt. Similar to a user change interrupt for the sync client 206, a user change interrupt for the sync engine 306 occurs when the user enters a change into the database 302 using the data application 304. The data application 304 sends the user change to the sync engine 306 in the form of a user change interrupt.

Again similar to the timer interrupt for the sync client 206, a timer interrupt for the sync engine 306 occurs when a synchronization timer expires, indicating that a previously-configured timing criterion for an automatic synchronization has occurred.

Another synchronization event that may occur is a client change interrupt. Similar to an engine change interrupt for the sync client 206, a client change interrupt indicates that the sync client 206 has initiated a synchronization process. When the sync client 206 initiates a synchronization process, it sends a data packet to the sync server 112, which is received by the sync engine 306. When the sync engine 306 determines that the data packet contains changes from the sync client 206, a client change interrupt is detected.

At the step 1106, if the next interrupt is a user change, the method proceeds to a step 1108. If the next interrupt is a timer interrupt, the method proceeds to a step 1112. If the next interrupt is a client change, the method proceeds to the step 800.

At the step 1108, the sync engine 306 enters the user change into the dataset 302, along with synchronization data, such as a timestamp and an indication that the user change is fresh. The method of FIG. 11 then proceeds to a step 1110. At the step 1110, the sync engine 306 determines whether the user change should be immediately synchronized to the dataset 202. Similar to the earlier description of immediate synchronization for the sync client 206, a user change may be immediately synchronized by the sync engine 306 with the dataset 202 based on various preset criteria. If the current user change satisfies the criteria for immediate synchronization, then the method of FIG. 11 proceeds to the step 900. Otherwise, the sync engine 306 returns to the step 1106. As described above, with reference to FIG. 9, the step 900 is a method for the sync engine 306 to send changes to the sync client 206. After the step 900, the sync engine 306 returns to the step 1106.

If the next interrupt received by the sync engine 306 is a timer interrupt, the sync engine 306 advances to the step 1112. At the step 1112, the sync engine 306 determines if there are any fresh changes to be sent to the sync client 206. If there are fresh changes, the sync engine 306 advances to the step 900 to perform the method of FIG. 9 for sending changes to the sync client 206. After the step 900, the sync engine 306 returns to the step 1106. Also, if there were no fresh changes at the step 1112, the sync engine 306 returns to the step 1106.

If the next interrupt received by the sync engine 306 is a client change interrupt, the sync engine 306 advances to the step 800 to perform the method of FIG. 8 to receive changes from the sync client 206. After the step 800, the sync engine 306 returns to the step 1106.

When, during the method of FIG. 10, the sync client 206 performs the method of FIG. 5 for sending changes to the sync engine 306, the sync engine 306 detects a client change interrupt at the step 1106 of FIG. 11 and proceeds to the method of FIG. 8 for receiving changes from the sync client 206. Thus, the sync engine 306 again performs the method of FIG. 8 at the same time that the sync client 206 performs the method of FIG. 5. Similarly, when, during the method of FIG. 11, the sync engine 306 performs the method of FIG. 9 for sending changes to the sync client 206, the sync client 206 detects an engine change interrupt at the step 1006 of FIG. 10 and proceeds to the method of FIG. 6 for receiving changes from the sync engine 306. Thus, the sync client 206 again performs the method of FIG. 6 at the same time that the sync engine 306 perform the method of FIG. 9.

In the preferred embodiment of the present invention, the wireless device 102 is a wireless telephone 102A with limited processing capabilities in comparison to those of the sync server 112. As a result, conflict resolution and duplicate resolution is preferably done by the sync engine 306, and the sync client 206 automatically enters any changes that it receives from the sync engine 306, assuming that conflict resolutions and duplicate resolutions have already been performed. A problem could arise, however, in the methods of FIGS. 10 and 11 under this scenario. Assume that a user makes a first change to a specific record in the dataset 302 at a first time and later makes a second, conflicting change to the same record in the dataset 202. Assume further that neither of the user changes satisfy the requirements for automatic synchronization of the steps 1010 and 1110, and that the sync engine 306 receives a timer inters apt before the sync client 206 receives a timer interrupt. In this case, the sync engine 306 would initiate a synchronization before the sync client 206 initiates a synchronization. The sync engine 306 would send the first user change to the sync client 206 before it becomes aware of the second change at the sync client 206, and so the sync engine 306 would not be able to perform a conflict resolution between the two user changes. Under these circumstances, the sync client 206 would receive the user change from the sync engine 306 and automatically enter it into the dataset 202, overwriting the more recent second user change. This is generally an undesirable result.

This result may not occur, however, in situations where synchronizations occur quickly after changes are made, especially at the wireless device 102. So, if all changes are immediately synchronized at the step 1010, or if timer interrupts at the wireless device 102 occur frequently, then this undesirable situation may never arise. Alternatively, this situation can be avoided in several different ways. For example, instead of directly sending changes to the sync client 206, such as at the step 900 of FIG. 11, the sync engine 306 may send a message to the sync client 206 indicating that the sync engine 306 has one or more changes for the dataset 202. In response to this message, if the sync client 206 does not have any changes for the dataset 302, the sync client 206 may send an Action Retrieve Records object to the sync engine 306, and the sync engine 306 may respond by sending its change(s) to the sync client 206. If the sync client 206 does have changes for the dataset 302, the sync client 206 may first send its own changes to the sync engine 306, followed by an Action Retrieve Records object. In this case, the sync engine 306 would receive the changes from the sync client 206, perform conflict and duplicate resolutions, enter the changes from the sync client 206 that survived the resolutions into the dataset 302, and, in response to the Action Retrieve Records object, send its own changes that survived conflict and duplicate resolutions to the sync client 206. If, on the other hand, the wireless device 102 has sufficient resources so that the sync client 206 can perform its own conflict and duplicate resolutions, then the sync engine 306 could send its chances to the sync client 206 and rely on the sync client 206 to perform conflict and duplicate resolutions.

As another alternative, the sync client 206 may detect possible conflicts, without attempting to resolve the conflicts. For example, if the sync client 206 receives an Action Update Record object from the sync engine 306 the sync client 206 could determine if it has a change to the same record. If the sync client 206 does have a change to the same record, the sync client 206 could simply discard the change received from the sync engine 306 without entering it and without acknowledging it. The sync client 206 would then preferably send its own change for that record. The sync engine 306 would automatically resend its change related to that record until it receives all acknowledgement from the sync client 206. The sync client 206 would continue discarding the change from the sync engine 306 until after it receives an acknowledgment from the sync engine 306 that the sync engine 306 has received the change to that record from the sync client 206. As soon as the sync engine 306 receives the change from the sync client 206, the sync engine 306 will perform conflict and duplicate resolution between the two changes, and only resend its own change to that record if it survived the conflict and duplicate resolution. So, if the sync client 206 receives a change to that record from the sync engine 306, aster the sync engine 306 has acknowledged the change to that record from the sync client 206, then the sync client 206 can automatically enter the change. Similarly, if the sync client 206 receives an Action Delete Record object related to the same record that the sync client 206 has a change, then the sync client 206 can discard the change until the sync engine 306 acknowledges receipt of the change from the sync client 206. Also, if the sync client 206 receives an Action Insert Record object while the sync client 206 also has a new record, the sync client 206 should discard the change until the sync engine 306 acknowledges the change from the sync client 206. This will allow the sync engine 306 to eliminate the possibility of multiple records directed to the same subject matter in the datasets 202 and 302.

As indicated above, the methods of FIG. 4 and 7 are the preferred methods for a connection-oriented communication system, while the methods of FIG. 10 and 11 are the preferred methods for a connectionless communication system. However, any of the methods of FIGS. 4, 7, 10, and 11 can be used in either a connection-oriented communication system or a connectionless communication system. In fact, where a communication system provides both connection-or-oriented communications and connectionless communications, all of the methods may be used in different circumstances. For example, the methods of FIGS. 10 and 11 may be automatically initiated upon the occurrence of certain previously-configured timing criteria, and the methods of FIGS. 4 and 7 may be initiated upon user activation of a sync key on the wireless telephone 102A. That way, a user may manually force a complete synchronization of the datasets 202 and 302 at any time if the user wants to be sure that all changes have been synchronized, or the user can wait for the sync client 206 and the sync engine 306 to automatically synchronize the datasets 202 and 302 if it is not important that changes be immediately synchronized. Many other scenarios can be used for the initiation of the methods of FIGS. 4, 7, 10, 11.

In one embodiment of the present invention the sync engine 306 and the sync client 206 may use different aspects of the methods of FIGS. 4 through 11 at different times to synchronize the datasets 202 and 302, and the particular situations in which the different methods will be utilized may be selected by the user. The following text describes this embodiment in connection with an existing wireless network 104 that provides both connection-oriented and connectionless communication capabilities, in the form of a data call capability and a paging capability, respectively. The same methods can be implemented in other communication systems that provide both connection-oriented and connectionless communication capabilities, such as a wireless system that provides data calls and packet-switching data capabilities.

The sync client 206 and the sync engine 306 together support several modes of synchronization. In one class of synchronization modes, the sync client 206 initiates all synchronization activity. The methods of FIGS. 4 and 7 form an example of this class of synchronization mode. In another class of modes, the sync engine 306 is allowed also to initiate (e.g. push) some synchronization activity. The method of FIG. 11 is an example of this class of synchronization mode. The sync client 206 and the sync engine 306 together support and manage synchronization using either their connectionless capabilities or using their connection-oriented calling capabilities (e.g. cellular data calling capabilities) or using a combination of their connectionless and connection-oriented calling capabilities.

The sync engine 306 preferably keeps user-settable preference settings for how aggressively the sync engine 306 is to push fresh changes onto the sync client 206. The settings include the following:

Setting S1) respond to sync client 206—Here the sync engine 306 sends fresh changes to the sync client 206 upon request by the sync client 206. This setting relates to the method of FIG. 7, where the sync engine 306 sends changes to the sync client 206 at the step 900, in response to receiving a change request from the sync client at the step 712.

Setting, S2) time—The sync engine 306 sends fresh changes to the sync client 206 at prescribed times (e.g. non-peak usage hours), without waiting for a change request from the sync client 206. This setting relates to the timer interrupt portion of the method of FIG. 11 (i.e., the steps 1106, 1112, and 900).

Setting S3.) trickle—The sync engine 306 sends fresh changes to the sync client 206 whenever there is a fresh change in the dataset 302, again without waiting for a change request from the sync client 206. This setting relates to the user changes interrupt portion of the method of FIG. 11 (i.e., the steps 1106, 1108, 1110, and 900), except that, in this embodiment, all changes are immediately synchronized, and there is no need for the step 1110.

Setting S4) respond to operator initiation—The sync engine 306 sends fresh changes to the sync client 206 if specifically requested to by an operator with proper permissions (e.g. the user via a user interface into the sync engine 306 (such as using the Internet client 118 through the data application 304) or a system administrator, a service provider, or an information content provider).

Preferably, the above settings are independently settable. Preferably, by default, the sync engine 306 is set so that settings S1 and S4 are active, and settings S2 and S3 are not active, so that the sync engine 306 will send changes to the sync client 206 in response to a request from the sync client 206 or in response to an operator initiation, but not based on the timed or trickle modes. The sync engine 306 may allow the user to change these preference settings using the Internet client 118, through the Internet 108 and the data application 302, or using the wireless device 102, through the wireless network 104 and the WAP browser described above.

During operation, the sync engine 306 may detect a synchronization event or interrupt. This event may comprise a request for fresh changes (e.g. all, or an identified subset (e.g. identified by record identifier)) by the sync client 206, a timer's alarm, an entry of a fresh change in the dataset 302, or a request from an operator with permission. The sync engine 306 may then respond to the event by deciding to initiate sending fresh changes only if the settings allow such a response. The sync client 206 may request a change to the preference settings S1 to S4 in the same communication that it sends a request for fresh changes. In this way, the sync client 206 may request fresh changes from the sync engine 306 and specify the criteria that will be used by the sync engine 306 in determining when to send the requested changes. For example, the sync client 206 may send a request for fresh changes along with a request to set the preference setting S2 and to clear the other preference settings, so that the sync engine 306 will wait until a prescribed time before sending the fresh changes. As an alternative to allowing the 'setting' of the preference settings along with a request for fresh changes, the sync client 206 may specify the criteria that are to be used by the sync engine 306 in responding to that particular change request, without actually changing the settings, so that, after responding to that change request, the sync engine 306 returns to the previous preference settings to determine when to send subsequent changes to the sync client 206.

The sync engine 306 preferably keeps user-settable preference settings for how it should initiate sending of fresh changes to the sync client 206. The settings are as follows:

Setting H1) data call-push—The sync engine 306 simply calls the sync client 206 by directly 'dialing' and establishing a data call with the sync client 206 over which fresh changes may be pushed into the sync client 206. Dialing is simply dialing the sync client 206's 'phone number' or the like. This procedure is the same as the procedure described above in connection with the step 404 of FIG. 4, but in the opposite direction.

Setting H2) notify-requestcallback-push—The sync engine 306 notifies the sync client 206 of the existence of fresh changes on the dataset 302 by sending a paging message with a header that indicates that the message is from the sync engine 306 and requests that the client 'dial' the sync engine 306 (i.e., dial the sync engine 306's 'phone number' or the like). Preferably the header also indicates the number and size (e.g. number of bytes of information) of the fresh changes (and preferably also the identities of the changes e.g. last names for a contact dataset or event titles for a calendar dataset). This option may be helpful for customer billing purposes. For example, the sync engine 306 may be part of a service provided by a service provider, and if so, the sync engine 306 preferably uses a '900' phone number for itself such that if the sync client 206 calls the '900' phone number, then an additional per-minute charge can be automatically tabulated by the wireless network provider (e.g. cellular carrier), and the sync engine 306's service provider needs not perform separate billing for the service of maintaining the sync engine 306.

Setting H3) notify-requestpull—The sync engine 306 notifies the sync client 206 of the existence of fresh changes on the dataset 302 by sending a paging message with a header that indicates that the message is from the sync engine 306. Preferably the header also indicates the number and size (e.g. number of bytes of information and/or the number of records) of the fresh changes. Unlike H2, this setting does not request that sync client 206 phones the sync engine 306 back right away. Instead, the sync client 206 is left to reply with a pull (e.g. request to the sync engine 306 for fresh changes) at its (i.e., its user's) own leisure. This setting could comprise displaying an icon or message on the display 218 to signal to the user that the sync engine 306 has fresh changes for synchronization. The user may respond to this indication at any desired time to initiate synchronization.

Setting H4) page-push—The sync engine 306 simply sends one or more pages to the sync client 206 that contains the fresh changes.

Setting H5) auto-determine—The sync engine 306 automatically determines, from a set of rules, which of the choices H1, H2, H3, or H4 is the best choice given the circumstances. If setting H5 is set, the user may separately set a set of masks (e.g. flags) that exclude particular elements of H1, H2, or H4 from consideration. (H3 is the least obtrusive, and is preferably always allowed, at least as a last choice.) Preferably, the rules depend on (a) the current per-minute charge for data calls (e.g. peak hours versus non-peak hours), (b) the amount of fresh changes to be sent (e.g. the number of bytes), and (c) whether the changes are being sought to be sent in response to a user or sync client 206 request (e.g. via settings S1 or S4 by the user) as opposed to whether the changes are being sought to be sent by the sync engine 306 itself (e.g. via settings S2 or S3) or by an operator who is not the user (e.g. via setting S4 by not-the-user).

Preferably, the sync engine 306 includes exactly one of the preferences H1 to H5 to have been set as the preference setting for user-requested synchronizations or sync client 206-requested synchronizations. Preferably, the sync engine 306 includes exactly one of H1 to H5 to have been set as the preference setting for synchronizations, not by direct request from the user but rather by the sync engine 306's, or a non-user's (e.g. content provider's) own initiative. Preferably two sets of H5 masks may be set by the user, one set for user-requested synchronizations and one set for sync client 206-requested synchronizations.

As described above, if the setting H5 is set, the sync engine 306 will use a set of rules to determine which of the communication modes H1 to H4 will be used to send changes to the sync client 206. Under one rule, if there is a is user-requested or sync client 206-requested synchronization and if the amount of flesh changes is low (e.g. lower than a threshold), then the sync engine 306 chooses to use H4 (page-push). Conversely, if the amount of fresh changes is high (e.g. higher than a threshold), then the sync engine 306 chooses to use H1 or H2. (H2 is chosen if there is a billing or record-keeping reason to use H2.) If such a first-choice has been masked, H3 is chosen instead. Under another rule, if there is a sync engine 306-requested or nonuser-operator-requested synchronization and if the amount of fresh changes is low (e.g. lower than a threshold), then the sync engine 306 chooses to use H4 (page-push). Conversely, if the amount of flesh changes is high (e.g. higher than a threshold), then the sync engine 306 chooses to use H1 or H2. (H2 is chosen if there is a billing or record-keeping reason to use H2.) If these choices have been masked, H3 is chosen.

The sync client 206 responds to the various actions H1, H2, H3, or H4 of the sync engine 306 as follows:

Response HR1) In response to the server's H1 action, the sync client 206 receives notice (e.g. a ringing signal from the cellular network) of a data call from the server. Preferably, the sync client 206 includes caller-identification functionality (which is well known by a person of ordinary skill in the relevant art) by which the sync client 206 can know even before answering the call that the call is a synchronization call. (By comparison to the sync engine 306's caller ID number (e.g. phone number) that is stored in the sync client 206.) As a result, because the sync client 206 has determined that the call is from the sync engine 306, the sync client 206 preferably suppresses ordinary phone ringing, and instead picks up the phone according to the following logic.

One possibility is that the sync client 206 has been set to pick up data calls from the sync engine 306 without question. This may always be the case (e.g. even for sync engine 306-pushed calls). Or, this setting may only be active for sync client 206-requested calls (e.g. calls from the sync engine 306 within a threshold amount of time from a request for changes from the sync client 206).

A first alternative to always picking up calls from the sync engine 306 without question is to let the phone ring, allow the user to pick it up, and at that time, obtain user permission to proceed, at which time the phone receives a signal from the sync engine 306 and the call is turned into a data call. The user permission to proceed, may be obtained by playing a 'say yes to proceed' or 'press 1 to proceed' prompt and awaiting and detecting the user's response (e.g. detecting a pressing of the 1 key or recognizing (using built-in speech recognition software or sync engine 306-based speech recognition software) that the user has said yes).

As a second alternative setting to answering calls from the sync engine 306 without question (either for sync engine 306-pushed calls or calls presumed to respond to sync client 206 requests), the sync client 206 may be set to use a type of 'reverse-ringing logic'. According to this logic, the sync client 206 includes a list of phone numbers (caller ID numbers), including the sync engine 306's number, preferably including only the sync engine 306's number. Any call detected by the sync client 206 to be from one of these numbers will be dealt with using 'reverse-ringing logic'. In particular, a different type of ring tone (e.g. an arbitrary.wav file) is used. When the user hears this 'reverse-logic' tone, the user knows that the phone will pick up the phone call automatically unless the user pushes a keypad button (e.g. a 'cancel' or similar button) (e.g. any button at all) or causes other user input. This keystroke or other input tells the sync client 206 to not pick up the call. Clearly, this logic is the opposite of ordinary phone behavior, in which a call is not picked up unless the user enters an input (e.g. keystroke).

Once the sync client 206 picks up a call from the sync engine 306, then it accepts and processes the changes as usual, e.g. as described above in connection with FIG. 6 and in the incorporated and commonly-owned U.S. patent application having Ser. No. 09/311,781, filed May 13, 1999.

Response HR2) In response to the sync engine's H2 action, the sync client 206 receives a page from the sync engine 306 that tells the sync client 206 that the sync engine 306 has fresh changes and that the sync engine 306 prefers a callback. In response to this page, the sync client 206 calls the sync engine 306 back and initiates as much synchronization as it wants to. The sync client 206 preferably calls back for full two-way synchronization, as described above in connection with FIGS. 4 and 7.

Response HR3) In response to the sync engine's H3 action, the sync client 206 receives a page from the sync engine 306 that tells the sync client 206 that the sync engine 306 has flesh changes (and the amount of such changes and the identities of the changed records). At this point, the sync client 206 can respond essentially in the same way as HR2, except that the sync client 206 feels less 'urgency' from the sync engine 306 and therefore may feel less compelled to call back right away. The sync client 206 may also simply page back instead of call back.

Response HR4) In response to the sync engine's H4 action, the sync client 206 receives a page containing fresh changes from the sync engine 306, and processes the page in the usual manner—i.e., the sync client 206 propagates the changes in the page as appropriate, as described above in connection with the method of FIG. 6 and in the incorporated and commonly-owned U.S. patent application having Ser. No. 09/311,781, U.S. Pat No. 6,487,560 filed May 13, 1999.

In HR2, HR3, and HR4, the sync client 206 receives a page from the sync engine 306. Preferably, the sync client 206 handles all such pages in a consistent manner. Note first that the sync client 206 includes a directory structure or 'folder structure' for received messages. See for example, the message directories within the PageWriter™ pager from Motorola, Inc. Upon receiving a page, the sync client 206 inspects the header to look for a special identifier. (e.g. string) that shows that the page is from the sync engine 306. If the page is from the sync engine 306, the sync client 206 puts a 'page summary' (containing the number of changes, etc.) into a 'synchronization' message folder seen by the user, and when the user reviews the page summary, the user can either manually respond to the page as necessary (e.g. initiate sync, call back, etc.), or the sync client 206 can automatically respond to the page.

All of the user preference settings described above relative to the sync engine 306 may also be implemented for the sync client 206 in similar manner. However, the sync client 206 is preferably given more control over how and when synchronizations will occur between the sync client 206 and the sync engine 306. One reason for this is that the wireless device 102 is generally under more direct control of a user than the sync server 112, so giving more control to the sync client 206 effectively gives more control to the user. Another reason is that the sync server 112 preferably has greater processing capabilities than the wireless device 102, so giving more control to the sync client 206 enables the sync client 206 to initiate synchronization only when sufficient resources are available at the wireless device 102, such as when the user of the wireless device 102 is not involved in a different activity, such as a voice telephone call.

So, while all of the user preference settings of the sync engine 306 may be implemented for the sync client 206, the invention may also be implemented by providing the sync client 206 with only a subset of the user preference settings of the sync engine 306. For example, the sync client 206 may be given the settings S2, S3, and S4, so that it can send fresh changes to the sync engine 306 upon the occurrence of a timer interrupt, a user input of a fresh change, or a user activation of a synchronization function, but without enabling the sync client 206 to respond to a request for fresh changes from the sync engine 306.

Similarly, all of the communication modes H1 to H5 may also be implemented in the sync client 206 in a similar manner. Again, however, the present invention may also be implemented without providing all of these possible modes to the sync client 206. In particular, the modes H2 and H3 need not be implemented for the sync client 206. The modes H1 and H4 give more control to the sync client regarding the timing of synchronizations between the sync client 206 and the sync engine 306.

The rules for implementing the option H5 in the sync client 206 will also preferably to give greater control of the timing and mode of synchronizations to the sync client 206. In one embodiment for example, only the settings H1 and H4 are selected. If the amount of fresh changes is low, then the sync client 206 chooses to use H4, while, if the amount of fresh changes is high, then the sync client 206 chooses to use H1.

The responses by the sync engine 306 to the synchronization options provided to the sync client 206 may also be similar to the responses by the sync client 206 to the synchronization options provided to the sync engine 306, except that, under the response HR1, the sync engine 306 will preferably always pick up calls from the wireless device 102, instead of the two alternatives of either obtaining user permission to proceed or using the "reverse-ringing logic." Thus, the response HR1 for the sync engine 306, that is the response by the sync engine 306 to a data call-push from the sync client 206 may comprise the method of FIG. 7, with or without the steps 712 and 900. The response HR4 for the sync engine 306 may comprise the steps 1106 and 800 of the method of FIG. 11. The responses HR2 and HR3 for the sync engine 306 will be similar to the responses HR2 and HR3 for the sync client 206, but in the opposite direction.

While the invention is described in some detail with specific reference to a preferred embodiment and certain alternatives, there is no intent to limit the invention to that particular embodiment or those specific alternatives. Thus, the true scope of the present invention is not limited to any one of the foregoing exemplary embodiments but is instead defined by the appended claims.

What is claimed is:

1. A method of synchronizing data values between a first device and a second device, the second device comprising a second dataset, the first device having a first plurality of data value changes to the second dataset and the second device having a second plurality of data value changes to the second dataset, the method comprising the steps of:

establishing a communication interface between the first device and the second device, the communication interface comprising a wireless interface;

repeating the following steps until the second device receives all of the first plurality of changes:
the first device sending to the second device one or more changes from the first plurality of changes that have not yet been received by the second device;
the second device sending a message to the first device acknowledging receipt of whichever changes the second device actually receives; and
the first device determining which, if any, of the first plurality of changes have not yet been received by the second device, based on the acknowledgement message from the second device;

the second device resolving conflicts between the first plurality of changes and the second plurality of changes;

the second device incorporating into the second dataset those changes from the first plurality of changes that survived the conflict resolution.

2. The method of claim 1, wherein the first device also comprises a first dataset and the method further comprises the steps of:

after the second device resolves conflicts between the first plurality of changes and the second plurality of changes, repeating the following steps until the first device receives all of the second plurality of changes that survived the conflict resolution:
the second device sending to the first device one or more changes from the second plurality of changes that survived the conflict resolution and that have not yet been received by the first device;
the first device sending a message to the second device acknowledging receipt of whichever changes the second device actually receives; and the second device determining which, if any, of the second plurality of changes that survived the conflict resolution have not yet been received by the first device, based on the acknowledgement message from the first device; and the first device incorporating into the first dataset the changes from the second device.

3. The method of claim 2, wherein the first dataset and the second dataset contain PIM data.

4. The method of claim 3, wherein the first device comprises a PIM application.

5. The method of claim 3, wherein the second device comprises a PIM application.

6. The method of claim 2, wherein the first device sends the acknowledgment message in response to an acknowledgment request sent from the second device to the first device.

7. The method of claim 2 further comprising the steps of the first device determining if a change received from the second device involves creating a new data record in the first device and, if so, sending a message to the second device indicating the record ID within the first device for the new data record.

8. The method of claim 2, wherein the first device and second device send changes and messages in the form of data packets, over a packet-switching network.

9. The method of claim 1, wherein the first device comprises a wireless device and the second device comprises a sync server.

10. The method of claim 1, wherein the second device sends the acknowledgment message in response to an acknowledgment request sent from the first device to the second device.

11. The method of claim 1 further comprising the step of the second device resolving duplicates between the first plurality of changes and the second plurality of changes.

12. The method of claim 1, wherein the first device initiates the synchronization in response to a user activating a key on the first device.

13. The method of claim 1, wherein the first device initiates the synchronization in response to a user entering a data value change.

14. The method of claim 1, wherein the first device initiates the synchronization in response to a timer interrupt.

15. The method of claim 1, wherein the first plurality of changes and the second plurality of changes are fresh changes.

16. A method for synchronizing a first set of changes that have been made to a first dataset in a wireless device with a second set of changes that have been made to a second dataset in a second device, the wireless device comprising a sync client and the second device comprising a sync engine, the method comprising:

the sync client establishing a communication interface with the sync engine, the communication interface comprising a wireless interface;

the sync client sending the first set of changes to the sync engine;

the sync engine performing a conflict resolution between the first set of changes and the second set of changes;

the sync engine entering those changes from the first set of changes that survived the conflict resolution into the second dataset;

the sync client sending a request for changes to the sync engine and, in response, the sync engine sending one or more changes from the second set of changes that survived the conflict resolution to the sync client;

the sync client entering the changes received from the sync engine into the first dataset.

17. The method of claim 16, wherein the step of the sync client sending the first set of changes to the sync engine comprises the following sub-steps:

repeating the following sub-steps until the sync engine receives all of the first set of changes:

the sync client sending to the sync engine one or more changes from the first set of changes that have not yet been received by the sync engine;

the sync engine sending a message to the sync client acknowledging receipt of whichever changes the sync engine actually receives; and the sync client determining which, if any, of the first set of changes have not yet been received by the sync engine, based on the acknowledgement message from the sync engine.

18. The method of claim 16, wherein the step of the sync engine sending one or more changes from the second set of changes to the sync client comprises the following sub-steps:

repeating the following sub-steps until the sync client receives all of the second set of changes to be sent:

the sync engine sending to the sync client one or more changes from the second set of changes that have not yet been received by the sync client;

the sync client sending a message to the sync engine acknowledging receipt of whichever changes the sync client actually receives; and the sync engine determining which, if any, of the second set of changes that are to be sent to the sync client have not yet been received by the sync client, based on the acknowledgement message from the sync client.

19. The method of claim 16, wherein the request for changes from the sync client specifies a number of changes that will be sent from the sync engine to the sync client.

20. The method of claim 16, wherein, before the sync client sends the first set of changes to the sync engine, the sync client determines whether a previous synchronization attempt was not completed successfully and, if a previous attempt was not completed successfully, completing the previous synchronization attempt.

21. The method of claim 16, wherein the wireless device is a wireless telephone with a PIM application, the second device is a sync server, and the first and second datasets comprise PIM data.

22. The method of claim 16, wherein the sync client initiates the synchronization method in response to a user selection of a synchronization function.

23. The method of claim 22, wherein the user selection of a synchronization function involves the user activating a key on the wireless device.

24. The method of claim 16, wherein the step of the sync client establishing a communication interface involves establishing a data call between the wireless device and the second device and wherein, after the sync client receives the changes from the sync engine, the sync client terminates the data call.

25. A method of synchronizing a first dataset in a first device with a second dataset in a second device, the method comprising the steps of:

establishing a communication interface between the first device and the second device;

in response to the first device receiving a first change to the first dataset, the first device sending the first change to the second device, the second device performing a conflict resolution between the first change and the second dataset and, if the first change survives the conflict resolution, the second device entering the first change into the second dataset; and in response to the second device receiving a second change to the second dataset that should also be made to the first dataset, the second device sending the second change to the first device and the first device entering the second change into the first dataset.

26. The method of claim 25, wherein the first change is received by the first device from a user of the first device.

27. The method of claim 25, wherein the second change is received by the second device from a user of the second device.

28. The method of claim 25, wherein the second change is received by the second device from a third device, during a synchronization with the third device.

29. The method of claim 25, wherein the communication interface comprises a packet-switching data network.

30. The method of claim 26, wherein the communication interface comprises a wireless interface.

31. The method of claim 25, wherein the first change is sent after the first device is no longer in use.

32. The method of claim 25, wherein the first change is sent after a preset time interval has expired.

33. The method of claim 25, wherein the first change is sent substantially immediately after the first change is received by the first device if the first change is of a first type, or the first change is sent after a delay if the first change is of a second type.

34. The method of claim 25, wherein the first change is sent in response to a user of the first device activating a synchronization function.

35. The method of claim 25, wherein the second change is sent after the second device is no longer in use.

36. The method of claim 25, wherein the second change is sent after a preset time interval has expired.

37. The method of claim 25, wherein the second change is sent in response to a user of the second device activating a synchronization function.

38. The method of claim 25, wherein, in response to the second change being made to the second dataset, the second device sends a message to the first device indicating that the second device has a change for the first dataset and awaits a message from the first device requesting that the second device send the change, before the second device sends the second change to the first device.

39. A method of synchronizing a first dataset in a first device with a second dataset in a second device, the method comprising the steps of:

establishing a communication interface between the first device and the second device;

in response to a first change being made to the first dataset, the first device sending the first change to the second device, the second device performing a conflict resolution between the first change and the second dataset and, if the first change survives the conflict resolution, the second device entering the first change into the second dataset; and in response to a second change being made to the second dataset, the second device sending the second change to the first device, the first device performing a conflict resolution between the second change and the first dataset and, if the second change survives the conflict resolution, the first device entering the second change into the first dataset.

* * * * *